US006646179B1

(12) United States Patent
Melius et al.

(10) Patent No.: US 6,646,179 B1
(45) Date of Patent: *Nov. 11, 2003

(54) ABSORBENT COMPOSITE

(75) Inventors: Mark Kevin Melius, Appleton, WI (US); Sandra Marie Yarbrough, Menasha, WI (US); Melissa Christine Putzer, Oshkosh, WI (US); Stanley Roy Kellenberger, Appleton, WI (US); Shannon Kathleen Byerly, Appleton, WI (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/773,716

(22) Filed: Dec. 20, 1996

Related U.S. Application Data

(60) Division of application No. 08/621,390, filed on Mar. 25, 1996, now Pat. No. 5,601,542, which is a continuation of application No. 08/145,452, filed on Oct. 29, 1993, now abandoned, which is a continuation-in-part of application No. 08/016,312, filed on Feb. 24, 1993, now abandoned.

(51) Int. Cl.[7] .......................... A61F 13/15; A61F 13/20
(52) U.S. Cl. ........................ 604/368; 604/358
(58) Field of Search .................... 604/367–368, 604/358, 372, 378, 385.1, 385.01

(56) References Cited

U.S. PATENT DOCUMENTS

| 2,331,271 A | 10/1943 | Gilchrist |
| 2,761,449 A | 9/1956 | Bletzinger |
| 2,810,716 A | 10/1957 | Markus |
| 2,952,260 A | 9/1960 | Burgeni |
| 2,955,641 A | 10/1960 | Burgeni |

(List continued on next page.)

FOREIGN PATENT DOCUMENTS

CA     1104002     6/1981

(List continued on next page.)

OTHER PUBLICATIONS

Richman, Edward et al., "New Super–Absorbent Sheet From Developments," *INDA Technical Symposium Book of Papers*, Mar. 19–21, 1980, pp. 77–87.

Turek et al., Dr. Wolfgang, "Testing of Superabsorbents—Supposition for Their Appropriate Application in Disposables," *Insight '82: Absorbent Products Conference*, Oct. 13–14, 1982, Section IV, pp. 1–17.

Mizutani, Hiroshi, "Design of Japanese Baby Diapers," *Insight '87: Absorbent Products Conference*, Sep. 23–24, 1987, Section VIII, pp. 1–12.

(List continued on next page.)

*Primary Examiner*—K. M. Reichle
(74) *Attorney, Agent, or Firm*—Brinks Hofer Gilson & Lione

(57) ABSTRACT

An absorbent composite suitable for use in a disposable absorbent garment includes material for containing a superabsorbent material and a supersbsorbent material contained by said containment material. The superabsorbent material has a Pressure Absorbency Index of at least 100 and a 16-hour extractable level of less than about 13 weight percent; a Pressure Absorbency Index of at least 100 and a Vortex Time of less than about 45 seconds; or a Pressure Absorbency Index of at least about 110. The superabsorbent material is present in the containment means in an amount of from about 30 to about 100 weight percent based on total weight of the containment material and the superabsorbent material. A disposable absorbent garment includes an outer cover, a body-side liner, and an absorbent composite such as that described above.

6 Claims, 5 Drawing Sheets

U.S. PATENT DOCUMENTS

| | | |
|---|---|---|
| 3,016,599 A | 1/1962 | Perry, Jr. |
| 3,017,304 A | 1/1962 | Burgeni |
| 3,060,936 A | 10/1962 | Burgeni |
| 3,070,095 A | 12/1962 | Torr |
| 3,308,826 A | 3/1967 | Blake |
| 3,347,236 A | 10/1967 | Torr |
| 3,369,544 A | 2/1968 | Crockford |
| 3,494,362 A | 2/1970 | Burgeni |
| 3,523,536 A | 8/1970 | Ruffo |
| 3,589,364 A | 6/1971 | Dean et al. |
| 3,592,194 A | 7/1971 | Duncan |
| 3,595,235 A | 7/1971 | Jespersen |
| 3,612,055 A | 10/1971 | Mesek et al. |
| 3,663,348 A | 5/1972 | Liloia et al. |
| 3,665,921 A | 5/1972 | Stumpf |
| 3,669,103 A | 6/1972 | Harper et al. |
| 3,670,731 A | 6/1972 | Harmon |
| 3,730,184 A | 5/1973 | Mesek |
| 3,768,118 A | 10/1973 | Ruffo et al. |
| 3,768,480 A | 10/1973 | Mesek et al. |
| 3,772,417 A | 11/1973 | Vogt |
| 3,810,468 A | 5/1974 | Harper et al. |
| 3,890,974 A | 6/1975 | Kozak |
| 3,901,236 A | 8/1975 | Assarsson et al. |
| 3,903,889 A | 9/1975 | Torr |
| 3,926,891 A | 12/1975 | Gross et al. |
| 3,935,099 A | 1/1976 | Weaver et al. |
| 3,954,721 A | 5/1976 | Gross |
| 3,997,484 A | 12/1976 | Weaver et al. |
| 4,028,290 A | 6/1977 | Reid |
| 4,051,086 A | 9/1977 | Reid |
| 4,055,180 A | 10/1977 | Karami |
| 4,062,817 A | 12/1977 | Westerman |
| 4,069,177 A | 1/1978 | Smith |
| 4,076,663 A | 2/1978 | Masuda et al. |
| 4,090,013 A | 5/1978 | Ganslaw et al. |
| 4,102,340 A | 7/1978 | Mesek et al. |
| 4,103,062 A | 7/1978 | Aberson et al. |
| 4,104,214 A | 8/1978 | Meierhoefer |
| 4,105,033 A | 8/1978 | Chatterjee et al. |
| 4,128,692 A | 12/1978 | Reid |
| 4,144,886 A | 3/1979 | Holst et al. |
| 4,155,893 A | 5/1979 | Fujimoto et al. |
| 4,167,464 A | 9/1979 | George |
| 4,190,562 A | 2/1980 | Westerman |
| 4,191,672 A | 3/1980 | Salome et al. |
| 4,200,557 A | 4/1980 | Chatterjee et al. |
| 4,224,366 A | 9/1980 | McCabe, Jr. |
| 4,242,408 A | 12/1980 | Evani et al. |
| 4,260,443 A | 4/1981 | Lindsay et al. |
| 4,269,188 A | 5/1981 | Nishizawa et al. |
| 4,286,082 A | 8/1981 | Tsubakimoto et al. |
| 4,297,410 A | 10/1981 | Tsuchiya et al. |
| 4,327,728 A | 5/1982 | Elias |
| 4,333,462 A | 6/1982 | Holtman et al. |
| 4,333,463 A | 6/1982 | Holtman |
| 4,340,556 A | 7/1982 | Ciencewicki .............. 264/119 |
| 4,340,706 A | 7/1982 | Obayashi et al. |
| 4,357,827 A | 11/1982 | McConnell |
| 4,360,021 A | 11/1982 | Stima |
| 4,381,320 A | 4/1983 | Nguyen |
| 4,381,782 A | 5/1983 | Mazurak et al. ............ 604/368 |
| 4,381,783 A | 5/1983 | Elias ......................... 604/368 |
| 4,389,487 A | 6/1983 | Ries ........................ 435/273 |
| 4,397,644 A | 8/1983 | Matthews et al. ......... 604/378 |
| 4,411,660 A | 10/1983 | Dawn et al. ............... 604/396 |
| 4,414,255 A | 11/1983 | Tokuyama et al. ......... 428/154 |
| 4,429,001 A | 1/1984 | Kolpin et al. ............. 428/283 |
| 4,449,977 A | 5/1984 | Korpman .................. 604/366 |
| 4,461,621 A | 7/1984 | Karami et al. ............. 604/368 |
| 4,473,689 A | 9/1984 | Login et al. |
| 4,497,772 A | 2/1985 | Mizuhara ................... 420/457 |
| 4,500,315 A | 2/1985 | Pieniak et al. ............. 604/379 |
| 4,535,098 A | 8/1985 | Evani et al. ............... 521/149 |
| 4,537,590 A | 8/1985 | Pieniak et al. ............. 604/379 |
| 4,540,454 A | 9/1985 | Pieniak et al. ............. 156/62.2 |
| 4,558,100 A | 12/1985 | Kightlinger et al. |
| 4,559,050 A | 12/1985 | Iskra ........................ 604/368 |
| 4,559,051 A | 12/1985 | Hanson ..................... 604/385 |
| 4,560,372 A | 12/1985 | Pieniak ..................... 604/369 |
| 4,573,988 A | 3/1986 | Pieniak et al. ............. 604/379 |
| 4,590,114 A | 5/1986 | Holtman ................... 428/171 |
| 4,596,567 A | 6/1986 | Iskra ........................ 604/368 |
| 4,604,313 A | 8/1986 | McFarland et al. ......... 428/172 |
| 4,605,401 A | 8/1986 | Chmelir et al. ............ 604/368 |
| 4,605,402 A | 8/1986 | Iskra ........................ 604/368 |
| 4,610,678 A | 9/1986 | Weisman et al. ........... 604/368 |
| 4,640,810 A | 2/1987 | Laursen et al. ............. 264/518 |
| 4,645,789 A | 2/1987 | Dabi |
| 4,650,127 A | 3/1987 | Radwanski et al. |
| 4,650,479 A | 3/1987 | Insley ....................... 604/358 |
| 4,654,039 A | 3/1987 | Brandt et al. ............... 604/368 |
| 4,655,757 A | 4/1987 | McFarland et al. ......... 604/366 |
| 4,666,975 A | 5/1987 | Yamasaki et al. ........... 524/733 |
| 4,673,402 A | 6/1987 | Weisman et al. ........... 604/368 |
| 4,677,174 A | 6/1987 | Alexander et al. |
| 4,699,619 A | 10/1987 | Bernardin .................. 604/378 |
| 4,699,620 A | 10/1987 | Bernardin .................. 604/385 |
| 4,699,823 A | 10/1987 | Kellenberger et al. ...... 428/219 |
| 4,710,187 A | 12/1987 | Boland et al. .............. 604/385 |
| 4,731,067 A | 3/1988 | Le-Khac .................... 604/367 |
| 4,734,478 A | 3/1988 | Tsubakimoto et al. ...... 527/300 |
| RE32,649 E | 4/1988 | Brandt et al. ............... 604/368 |
| 4,740,528 A | 4/1988 | Garvey et al. .............. 521/128 |
| 4,742,086 A | 5/1988 | Masamizu et al. ........... 521/62 |
| 4,755,178 A | 7/1988 | Insley et al. ................ 604/367 |
| 4,755,562 A | 7/1988 | Alexander et al. .......... 525/113 |
| 4,762,521 A | 8/1988 | Roessler et al. ............. 604/38 |
| 4,770,656 A | 9/1988 | Proxmire et al. ........... 604/393 |
| 4,773,903 A | 9/1988 | Weisman et al. ........... 604/368 |
| 4,788,237 A | 11/1988 | Le-Khac .................... 524/55 |
| 4,798,603 A | 1/1989 | Meyer et al. ............... 604/378 |
| 4,813,945 A | 3/1989 | Le-Khac .................... 604/367 |
| 4,820,773 A | 4/1989 | Alexander et al. .......... 525/274 |
| 4,833,222 A | 5/1989 | Siddell et al. ............... 526/200 |
| 4,834,735 A | 5/1989 | Alemany et al. ............ 604/368 |
| 4,847,141 A | 7/1989 | Pazos et al. ................ 428/226 |
| 4,880,868 A | 11/1989 | Le-Khac .................... 524/549 |
| 4,880,886 A | 11/1989 | Kondo et al. ................ 526/80 |
| 4,892,533 A | 1/1990 | Le-Khac .................... 604/368 |
| 4,923,454 A * | 5/1990 | Seymour et al. ............ 604/368 |
| 4,927,582 A | 5/1990 | Bryson ...................... 264/113 |
| 4,988,344 A | 1/1991 | Reising et al. .............. 604/368 |
| 4,988,345 A | 1/1991 | Reising ..................... 604/368 |
| 5,021,050 A | 6/1991 | Iskra ........................ 604/379 |
| 5,047,023 A | 9/1991 | Berg ......................... 604/368 |
| 5,061,259 A | 10/1991 | Goldman et al. ........... 604/368 |
| 5,082,723 A | 1/1992 | Gross et al. ................ 428/283 |
| 5,128,082 A | 7/1992 | Makoui ..................... 264/112 |
| 5,147,343 A | 9/1992 | Kellenberger ............... 604/368 |
| 5,149,335 A | 9/1992 | Kellenberger et al. ...... 604/372 |
| 5,192,606 A | 3/1993 | Proxmire et al. ........... 428/284 |
| 5,196,456 A | 3/1993 | Nguyen et al. .............. 522/81 |
| 5,314,420 A | 5/1994 | Smith et al. ................ 604/358 |
| 5,364,382 A * | 11/1994 | Latimer et al. |
| 5,411,497 A * | 5/1995 | Tanzer et al. ............... 604/368 |
| 5,425,725 A * | 6/1995 | Tanzer et al. |
| 5,433,715 A * | 7/1995 | Tanzer et al. |
| 5,509,905 A * | 4/1996 | Hanson et al. |

| | | | |
|---|---|---|---|
| 5,520,673 A | * | 5/1996 | Yarbrough et al. |
| 5,593,399 A | * | 1/1997 | Tanzer et al. |
| 5,601,542 A | * | 2/1997 | Melius et al. |
| 5,695,458 A | * | 12/1997 | Sosalla |

FOREIGN PATENT DOCUMENTS

| | | |
|---|---|---|
| DE | 2222780 | 11/1973 |
| DE | 3313344 | 10/1984 |
| DE | 3523617 | 1/1986 |
| EP | 0022792 | 1/1981 |
| EP | 0077510 | 4/1983 |
| EP | 0108637 | 5/1984 |
| EP | 0122042 | 10/1984 |
| EP | 0198683 | 10/1986 |
| EP | 0202125 | 11/1986 |
| EP | 0202127 | 11/1986 |
| EP | 0205674 | 12/1986 |
| EP | 0210968 | 2/1987 |
| EP | 0212618 | 3/1987 |
| EP | 0217032 | 4/1987 |
| EP | 0242478 | 10/1987 |
| EP | 0248963 | 12/1987 |
| EP | 0254476 | 1/1988 |
| EP | 0258120 | 3/1988 |
| EP | 0272682 | 6/1988 |
| EP | 0278601 | 8/1988 |
| EP | 0304319 | 2/1989 |
| EP | 0318989 | 6/1989 |
| EP | 0336578 | 10/1989 |
| EP | 0339461 | 11/1989 |
| EP | 0422504 | 4/1991 |
| EP | 0443627 | 8/1991 |
| EP | 0532002 | 3/1993 |
| EP | 0539703 | 5/1993 |
| FR | 2293914 | 7/1976 |
| GB | 719330 | 12/1954 |
| GB | 1500299 | 2/1978 |
| GB | 2078527 | 1/1982 |
| GB | 2104932 | 3/1983 |
| GB | 2119384 | 11/1983 |
| GB | 2145661 | 4/1985 |
| GB | 2155020 | 9/1985 |
| GB | 2158718 | 11/1985 |
| GB | 2174037 | 10/1986 |
| JP | S55-4462 | 1/1980 |
| JP | 58-42602 | 3/1983 |
| JP | 58-042602 | 3/1983 |
| JP | 61-58657 | 3/1986 |
| JP | 63-99861 | 5/1988 |
| JP | 63-275607 | 11/1988 |
| JP | 63-275608 | 11/1988 |
| TW | 272937 | 3/1996 |
| WO | WO80/01455 | 7/1980 |
| WO | WO82/00147 | 1/1982 |
| WO | WO86/04070 | 7/1986 |
| WO | WO88/01282 | 2/1988 |

OTHER PUBLICATIONS

Carus, Dr. Edmund, "The Development and Uses of Superabsorbents in Incontinent Products," *Insight '80: Absorbent Products Conference*, Nov. 19–21, 1980, Section V, pp. 1–8.

Exhibit MP.9 from Affidavit of Manfred Plischke in the matter of EP 0 339 461 and in the matter of an Opposition by The Procter & Gamble Company—article entitled "Breathable Absorbent Disposables—Market Developments And The Future." James P. Hanson, *Nonwovens World*, Nov. 1986, pp. 102–108.

Exhibit MP.5 from Affidavit of Manfred Plischke in the matter of EP 0 339 461 and in the matter of an Opposition by The Procter & Gamble Company—article entitled "Impact Of Recent Baby Diaper Design Changes On Machine Runnability and Efficiency" by Randy Schaaf of Paper Converting Machinery Co., Insight 87 Conference, Sep. 23–24, 1987, Section XI, pp. 1–22.

Absorbent Products Conference, Insight 87 International Conferences, Sep. 23–24, 1987, (Toronto, Ontario, Canada). Section IV "Characterization of Pulpex® E–338 Thermally Bonded Absorbent Cores" by Dr. H. Dale Wilson of Hercules, Inc.

Nonwovens Business Conference, Insight 87 International Conference, Sep. 20–22, 1987, (Toronto, Ontario, Canada). Section X "Thermally Bonded Core—The Key to Value Added Absorbent Products" by Peter G. Bither, Director of Strategy, Hercules, Inc., pp. 1–36.

Nonwoven Technology—A Steppingstone to Growth, Technical Symposium of Sep. 13–15, 1983, held in Baltimore, MD, pp. 73–82 "Pore Size Distributions From Measurements Of Liquid Uptake and Retention," by Bernard Miller and Ilya Tyomkin, Textile Research Institute, Princeton, N.J.

Absorbent Products Conference—Insight 87 International Conferences, Sep. 23–24, 1987, (Toronto, Ontario, Canada), "Here Today, Gone Tomorrow—1987 Absorbent Markets Review," by James P. Hanson of Marketing/Technology Service, Inc., Section X, pp. 1–31.

K–C's response to Oppositions of EP 339 461, Response filed Sep. 1, 1994.

Preliminary decision of Opposition Board dated Jun. 1995.

Further submissions by Opponent Molnlycke filed Oct. 2, 1995.

Determination of the Pore Volume Distribution in Dry Formed Fibrous Networks by Lars Wagberg and Bengt Widberg. Project 90, SCA Research AB. Report dated Jun. 1, 1990.

Further submissions by Opponent Stockhausen filed Sep. 29, 1995 (English translation included) with attached declaration of Dr. Dahmen and list of conference participants.

Further submission by Opponent Procter & Gamble filed Sep. 28, 1995, in preparation for oral proceedings on Nov. 30, 1995.

Reply by Kimberly–Clark filed Nov. 18, 1995, with attached Exhibits and Affidavits as referenced in the reply.

Reply by Kimberly–Clark filed Oct. 2, 1995, with attached information on "Capillary Suction Under Pressure."

Declaration by Berith Porso on behalf of the opponent Molnlycke AB, dated Sep. 18, 1995.

Declaration by Douglas R. Chambers on behalf of the opponent Molnlycke AB, dated Sep. 20, 1995.

Declaration of Hubert H. Fowler on behalf of the opponent Molnlycke AB, dated Sep. 20, 1995.

Graph based on data in patentee's EPO response of Sep. 1, 1994.

Affidavit of Hiroyuki Tanji, Group Leader of Overseas Group of R&D for Uni–Charm Corporation, dated Sep. 29, 1995.

Chart showing analytical result of super absorbent polymer, dated Jan. 6, 1998.

Instructions for Absorption Capacity Under Load and Re–absorption Capacity.

"Particle Size Table Sieve Information" chart and "Particle Size Distribution" chart dated Apr. 24, 1987.

Declaration by Peter Blomstrom on behalf of the opponent Molnlycke AB, dated Oct. 1995.

Affidavit of Stephen Allen Goldman in the matter of European Patent No. 0 339 461 and in the matter of an Opposition by the Procter & Gamble Company, filed Sep. 1995 (EPO).

Second Affidavit of Stephen Allen Goldman with attached Exhibits from laboratory notebook, filed Sep. 1995 with European Patent Office (EPO).

Affidavit of Dr. Manfred Plischke in the Matter of European Patent No. 0 339 461 and in the Matter of an Opposition by the Procter & Gamble Company, with attached Exhibits, filed Sep. 1995 (EPO).

"Raw Data Volume" Referred to in Exhibit MP12 to the Affidavit of Manfred Plischke in the Matter of European Patent No. 0,339,451 and in the matter of an Opposition by The Procter & Gamble Co., filed Sep. 1995 (EPO).

Affidavit of Graham Kenneth Moore in the Matter of European Patent No. 0 339 461 and in the Matter of an Opposition by the Procter & Gamble Company, with attached Exhibits, filed Sep. 1995 (EPO).

U.S. Ser. No. 08/145,924 entitled Absorbent Article Which Includes Superabsorbent Material Located in Discrete Pockets Having an Improved Containment Structure, filed Oct. 29, 1993 in the name of R. W. Tanzer et al., Now U.S. Patent No. 5,411,497.

Information set forth in paragraphs numbered 1,2,3, and 4 of the Information Disclosure Statement (Dated Jul. 22, 1994) for which this Form PTO–1449 is an attachment.

U.S. Ser. No. 08/145,925 entitled Absorbent Article Which Includes Superabsorbent Material Located in Discrete Pockets Having Water–Sensitive and Water–Insensitive Containment Structures filed Oct. 29, 1993 in the name of R. W. Tanzer et al., Now U.S. Patent No. 5,433,715.

U.S. Ser. No. 08/145,927 entitled Absorbent Article Which Includes Superabsorbent Material and Hydrophilic Fibers in Discrete Pockets filed Oct. 29, 1993 in the name of R. W. Tanzer et al. Now U.S. Patent No. 5,425,725.

U.S. Ser. No. 08/145,926 entitled Absorbent Article Which Includes Superabsorbent Material Located in Discrete Elongate Pockets Placed in Selected Patterns filed Oct. 29, 1993 in the name of R. W. Tanzer et al., Now U.S. Patent No. 5,593,399.

U.S. Ser. No. 07/824,766 entitled Absorbent Structure Having Improved Fluid Surge Management and Product Incorporating Same filed Jan. 17, 1992 in the name of B. J. Matthews et al., Now U.S. 5,364,382.

U.S. Ser. No. 07/757,760 entitled Thin Absorbent Article Having Rapid Uptake of Liquid filed Sep. 11, 1991 (abandoned)in the name of W. D. Hanson et al., Now U.S. Patent No. 5,509,915.

U.S. Ser. No. 08/096,654 entitled Thin Absorbent Article Having Rapid Uptake of Liquid filed Jul. 22, 1993 in the name of W. D. Hanson et al., Now U.S. Patent No. 5,509, 915.

"Superabsorbents—Breaking the Cellulose Cost Performance Barrier"—Peter Maul et al. American Colloid Company, Insight Conference, Toronto, Canada, Aug. 1986.

"A Method for Evaluating Superabsorbent Specialty Polymers"—E. V. Painter, TAPPI Symposium, 1985 Nonwovens Symposium, Apr. 21–25, 1985.

"Capillary Sorption Equilibria in Fiber Messes"—A. A. Burgeni and C. Kapur, *Textile Research Journal*, vol. 37, No. 5, pp. 356–366, May 1967.

"Letter from Nippon Gohsei to Stockhausen GmbH" dated Sep. 28, 1993.

"Copy of Invoice 10/87" (Ref. D10 from Stockhausen opposition of EP 339,461).

"Copy of Invoice 2/88" (Ref. D11 from Stockhausen opposition of EP 339,461).

"Copy of Invoice 3/88" (Ref. D12 from Stockhausen opposition of EP 339,461).

Bench Evaluation of Stockhausen Favor SAB Special Samples Nov. 11, 1987.

"Dubbel Taschenbuch fur den Maschinenbeu" vol. 1, corrected new edition of the 13th edition, Berlin, 1974, p. 903 Table "Prufsiebe".

Opposition of EP 339 461 B1 by Stockhausen, Oct. 19, 1993.

Opposition of EP 339 461 B1 by Procter & Gamble, Oct. 15, 1993.

Opposition of EP 339 461 B1 by Molnlycke, Oct. 20, 1993.

Opposition of EP 339 461 B1 by V. P. Schickedenz, Oct. 20, 1993.

"Determination of the Fluid Capacity of Some Commercial Catamenial Tampons", by M. Louis Arin, Ph.D., U.S. Food and Drug Administration, Winchester Engineering and Analytical Center, Winchester, MA 01890—Mar. 14–15, 1985.

"The Concept of Superabsorbent Polymer," by Dr. F. Masuda of Sanyo Chemical Industries Ltd. presented as Paper No. 13 at the Pira Fibramerics Program held Dec. 1–3, 1987.

Arakawa Technical Data by Arakawa Chemical (USA) Inc., 625 N. Michigan Ave., Suite 1700, Chicago, IL 60611— "Absorbency of Absorbent Polymer Under Pressure".

Aquareserve Technical Note by Nippon Gohsei—"High Water Absorbing Synthetic Resin" Technical Note 3—Approx. Summer Of 1987.

Lichstein, Bernard M., Ph.D., "Absorbency Characteristics, Mechanism and Measurement"; *1983 International Dissolving and Specialty Pulps Conference* (Apr. 5–8, 1983); pp. 143–147.

Martinis et al.; "Absorption of Liquids by Dry Fiber Networks"; *Proceedings of the Technical Association of the Pulp and Paper Industry;* 1981 Annual Meeting (Mar. 2–5, 1981); pp. 133–140.

Painter, E.V.; "Characterizing Absorbent Materials"; Association of the Nonwoven Fabrics Industry; Papers presented at Technical Symposium May 22–23, 1984; pp. 189 et seq.

Shishoo, Dr. Roshan L.; "New Methods of Testing Absorbent Type Aids for Adult Incontinent Persons"; Swedish Institute for Textile Research, Section VI; Absorbent Products Conf., 9/81.

George, Dr. Paul J.; "Surpon™—A New Superabsorbent Polymer For Absorbent Products"; BF Goodrich Group; Section III, pp. 1–16; Absorbent Products Conf., Sep. 16–18, 1981.

Erickson, R.E.; "Absorbent Laminate for Low Bulk, High Capacity Personal Care Products"; Dow Chemical U.S.A.; Section VI, pp. 24; Absorbent Products Conf., Nov. 19–21, 1980.

Tuerk, Dr. Wolfgang; "Testing of Superabsorbents—Supposition for Their Appropriate Application in Disposables"; Stockhausen GMBH; pp. 1–17.

Hodgman, Charles D. (Editor); *Handbook of Chemistry and Physics;* Cleveland, Ohio, 1956; pp. 3112–3115.

Aberson, G. M.; "The Water Absorbency of Pads of Dry, Unbonded Fibers"; Special Technical Association Publication STAP No. 8; 1970; pp. 282–307, TAPPI Seminar, May 12–15, 1969.

Lichstein, Bernard M.; "Demand Wettability, A New Method For Measuring Absorbency Characteristics of Fabrics"; Johnson & Johnson; Technical Symposium, Mar. 5–6, 1974; pp. 129–142.

Chatterjee, Pronoy K.; *Absorbency*, Chpt. VI; Textile Science and Technology 7; 1985, pp. 197–216.

ASTM Designation: D 1921 – 89; "Standard Test Methods for Particle Size (Sieve Analysis) of Plastic Materials"; pp. 480–483.

Chemidel Corporation, Procedure No. 8006, Issue Date Feb. 1, 1986: Revision Date Nov. 12, 1986; GATS; "Gravimetric Absorbency Testing System", Kallmes, O. J. et al.

Mizutani, Hiroshi; "Designing Japanese Diapers Becomes a Growing Concern"; *Nonwovens World;* Nov. 1987, pp. 39–42.

Hanson, James P., "Developing Superabsorbent Products With Dynamic Testing;" *Nonwovens World;* May–Jun. 1986; pp. 130–135.

Dugdale, Thomas J.; "Novel Superabsorbent Fibers;" *Nonwovens World;* Feb. 1987; pp. 107–110.

"Baby Diaper Design Update—1987", Published by Marketing/Technology Service, Inc.; Oct. 1987.

Hanson, James P.; "Designing Better Superabsorbent Baby Diapers;" *Nonwovens World;* May–Jun. 1987; pp. 69–74.

Richman, Edward et al.; "New Super–Absorbent Sheet Form Developments;" National Starch & Chemical Corporation; Bridgewater, New Jersey; pp. 77–87.

"Akucell SW Absorbent Material;" *Enka Information;* Polymer/Feeding System/Sheet.

Enka Industrial Colloide, Enka; "Methods of Analysis for Akucell S–Grades"; Nov. 11, 1983; Sep. 14, 1983; Jul. 21, 1983.

Mizutani, Hiroshi; "Design of Japanese Baby Diapers;" KAO Corporation, Section VIII; pp. 1–12.

Carus, Dr. Edmund; "The Development and Uses of Superabsorbents in Incontinent Products;" Section V, pp. 1–8, Insight 80.

Heilweil, H.G. (Editor); "Determining Pore Size Distributions in Fibrous Materials;" Notes on Research—Textile Research Institute; No. 363, Apr. 1984, pp. 1–7.

Shimomura, Tadeo; "Superabsorbent Polymers for Disposable Diapers;" EDANA's 1988 Nordic Nonwovens Symposium; Jun. 7–8, 1988, pp. 240–254.

Kallmes, O. J. et al.; "The Gravimetric Absorbency Testing System;" *1985 Nonwovens Symposium;* pp. 231–235.

Shishoo, R., Swedish Institute for Textile Research; Mar. 1987 International Dissolving Pulps Conference, *TAPPI Proceedings;* pp. 211–227.

Turk, Dr. Wolfgang; "Testing Superabsorbents . . . Supposition for their Appropriate Applications in Disposables"; Allgemeiner Vliesstoff Report 6—1982.

Dederichs, Dr. Welburga; "Superabsorbent Polymers: Their Properties Alone and in Combination with Fluff Pulp;" The Pira Fibramerics Programme; pp. 1–25, Nov. 28–30, 1989.

Scovic, Richard J. et al.; "The Most Important Aspects of Diaper Performance;" Assoc. of Nonwoven Fabrics Industry; *Book of Papers;* Int'l Nonwoven Fabrics Conf. May 30–Jun. 2, 1989, pp. 517–531.

Hanson, J.; "How Thin is Thin?"; Index 87 Congress; Session C2—Hygiene Solutions; pp. 1–11; Mar. 31–Apr. 2, 1987.

Shishoo, Dr. R. L.; "Mechanisms of Liquid Distribution in Absorbent Products"; Index 87 Congress; Session C1—Hygiene Problems; pp. 1 et seq.; Mar. 31–Apr. 2, 1987.

Cusick, G. E. et al.; "Absorbent Incontinence Products;" *The Textile Institute;* Textile Progress, vol. 20, No. 3; pp. 1–36; 1990.

Further submission re the Opposition to the grant of European Patent 532,002, filed by opponent Nippon Shokubai Co., Ltd., dated Oct. 16, 2002 (Oct. 16, 2002).

Summons to attend hearing re Oppositions to the grant of European Patent 615,736, on Jan. 22, 2003, with preliminary opinion by EPO, dated Aug. 1, 2002 (Aug. 1, 2002).

Submissions by Nippon Shokubai Co., Ltd., filled Dec. 12, 2002, in preparation for oral proceedings re Oppositions to the grant of European Patent 615,736, on Jan. 22, 2003.

Submissions by SCA Hygiene Products AB, filed on Dec. 17, 2002, in preparation for oral proceedings re Oppositions to the grant of European Patent 615,736, on Jan. 22, 2003.

Submissions by the Procter & Gamble Company under Rule 71A EPC, filed on Dec. 20, 2002, in preparation for oral proceedings re Oppositions to the grant of European Patent 615,736, on Jan. 22, 2003.

Observations by Patentee on the Notices of Opposition to the grant of European Patent 761,191, together with a revised Annex 1 regarding document numbering, an annex title "Main Request" containing revised claims as proposed to be maintained, and the document D32, "Summary of Study –Home Use Disposable Diaper Testing", discussed in the main document, all filed in the EPO on Nov. 29, 2002.

Observations by Patentee on the Notices of Opposition to the grant of European Patent 761,192, together with a revised Annex 1 regarding document numbering, and an annex titled "Main Request" containing revised claims as proposed to be maintained, all filed in the EPO on Nov. 29, 2002.

* cited by examiner

ABSORBENT COMPOSITE

CROSS-REFERENCES TO RELATED APPLICATIONS

This is a division of application Ser. No. 08/621,390, filed Mar. 25, 1996, now U.S. Pat. No. 5,601,542; which is a continuation of application Ser. No. 08/145,452, filed Oct. 29, 1993, now abandoned; which is a continuation-in-part of application Ser. No. 08/016,312, filed Feb. 24, 1993, now abandoned; the contents of all of which are incorporated by reference.

BACKGROUND OF THE INVENTION

DESCRIPTION OF THE RELATED ART

Absorbent composites suitable for use in disposable absorbent garments such as diapers, adult incontinent products, and the like, are known. Such absorbent composites are described, for example, in U.S. Pat. No. 4,699,619 issued Oct. 13, 1987, to Bernardin; U.S. Pat. No. 4,798,603 issued Jan. 17, 1989, to Meyer et al.; U.S. Pat. No. 4,834,735 issued May 30, 1989, to Alemany et al.; U.S. Pat. No. 5,147,343 issued Sep. 15, 1992, to Kellenberger; and U.S. Pat. No. 5,149,335 issued Sep. 22, 1992, to Kellenberger et al.

Generally, such absorbent composites comprise a means of containing a high-absorbency material and a high-absorbency material. Suitable means for containing the high-absorbency material include fibrous matrixes, such as those formed from air-laid cellulosic fibers or a coform material comprising cellulosic fibers and meltblown polyolefin fibers. A wide variety of high-absorbency materials (also known as superabsorbent materials) are known to those skilled in the art. See, for example, U.S. Pat. No. 4,076,663 issued Feb. 28, 1978, to Masuda et al.; U.S. Pat. No. 4,286,082 issued Aug. 25, 1981, to Tsubakimoto et al.; U.S. Pat. No. 4,062,817 issued Dec. 13, 1977, to Westerman; and U.S. Pat. No. 4,340,706 issued Jul. 20, 1982, to Obayashi et al.

Many known absorbent composites comprising a high-absorbency material employ the high-absorbency material in relatively low concentrations. That is, many of the absorbent composites comprise airlaid. cellulosic fibers and less than about 20 weight percent of a high-absorbency material. This is due to several factors.

Many high-absorbency materials are unable to absorb a liquid at the rate at which the liquid is applied to the absorbent composites during use. Accordingly, a relatively high concentration of fibrous material is desirable to temporarily hold the liquid until the high-absorbency material can absorb it. Further, the fibers serve to separate the particles of high-absorbency material so that gel-blocking does not occur. Gel-blocking refers to the situation wherein particles of high-absorbency material deform during swelling and block the interstitial spaces between the particles, or between the particles and the fibers, thus preventing the flow of liquid through the interstitial spaces.

U.S. Pat. No. 5,147,343 issued Sep. 15, 1992, to Kellenberger describes an absorbent composite adapted to avoid the problem of gel-blocking. U.S. Pat. No. 5,147,343 describes the use of a superabsorbent material which can absorb at least 27 milliliters of a 0.9 weight percent aqueous sodium chloride solution per gram of superabsorbent material while the superabsorbent is under a restraining pressure of at least 21,000 dynes per square centimeter. When the superabsorbent material is in the form of discrete particles, at least about 50 percent by weight of the superabsorbent material has a size greater than the median pore size of the porous fiber matrix when wet. The described absorbent composites are said to contain up to about 90 weight percent of a superabsorbent material.

The presence of a relatively low concentration of high-absorbency material and a relatively greater concentration of fibrous materials has resulted in the production of absorbent composites which tend to be relatively thick. In some instances, the use of a relatively thick absorbent composite in a disposable absorbent garment is acceptable. However, in recent years it has become increasingly desirable to produce absorbent composites which are thin compared to the more traditional absorbent composites but which still possess the same absorbent capacity. The desire to produce relatively thin absorbent composites has resulted in the desire to incorporate ever-increasing amounts of high-absorbency material into the absorbent composites. This is because the absorbent capacity of such high-absorbency materials is generally many times greater than the absorbent capacity of fibrous materials. For example, a fibrous matrix of wood pulp fluff can absorb about 7–9 grams of a liquid, (such as 0.9 weight percent saline) per gram of wood pulp fluff, while the high-absorbency materials. can absorb at least about 15, preferably at least about 20, and often at least about 25 grams of liquid, such as 0.9 weight percent saline, per gram of the high-absorbency material.

U.S. Pat. No. 5,149,335 issued Sep. 22, 1992, to Kellenberger et al. is directed to an absorbent structure containing a relatively high concentration of superabsorbent material. Specifically, U.S. Pat. No. 5,149,335 describes the use of a superabsorbent material having certain absorbent characteristics when it is desired to employ the superabsorbent material at relatively high concentrations. Specifically, the superabsorbent material is described as having a 5-minute Absorbency Under Load value of at least about 15 grams per gram and a free-swell rate of less than about 60 seconds.

While absorbent composites containing a relatively high concentration of high-absorbency material are known, and are generally acceptable in use, it is desired to more particularly define absorbent composites containing a relatively high concentration of a high-absorbency material and those high-absorbency materials which are well suited for use in absorbent composites comprising a relatively high concentration of the high-absorbency material.

SUMMARY OF THE INVENTION

The present invention relates to a method of testing superabsorbent materials for thier suitability for use in absorbent composites to be included in disposable absorbent garments, the absorbent composites comprising from about 30 to about 100 weight percent of superabsorbent materials, the method comprising the steps of (a) determining the absorbency under load characteristics of the superabsorbent materials at restraining forces of 0.01, 0.29, 0.57, and 0.90 pounds per square inch, (b) determining the total of the absorbency under load characteristics at each said restraining force for each superabsorbent material, and (c) choosing as suitable a superabsorbent material for which the total of said absorbency under load characteristics is at least about 110.

It is preferred that a superabsorbent material is selected for which the total of said absorbency under load characteristics is at least about 120, and more preferred that a superabsorbent material is selected for which the total of said absorbency under load characteristics is at least about 140.

It is also preferred that a superabsorbent material is selected which has a 16-hour extractables level of less than about 13 weight percent, particularly of less than about 10 weight percent, more particularly of less than about 7 percent, and even more particularly of less than about 3 weight percent.

DETAILED DESCRIPTION OF A PREFERRED EMBODIMENT

Figure 1:
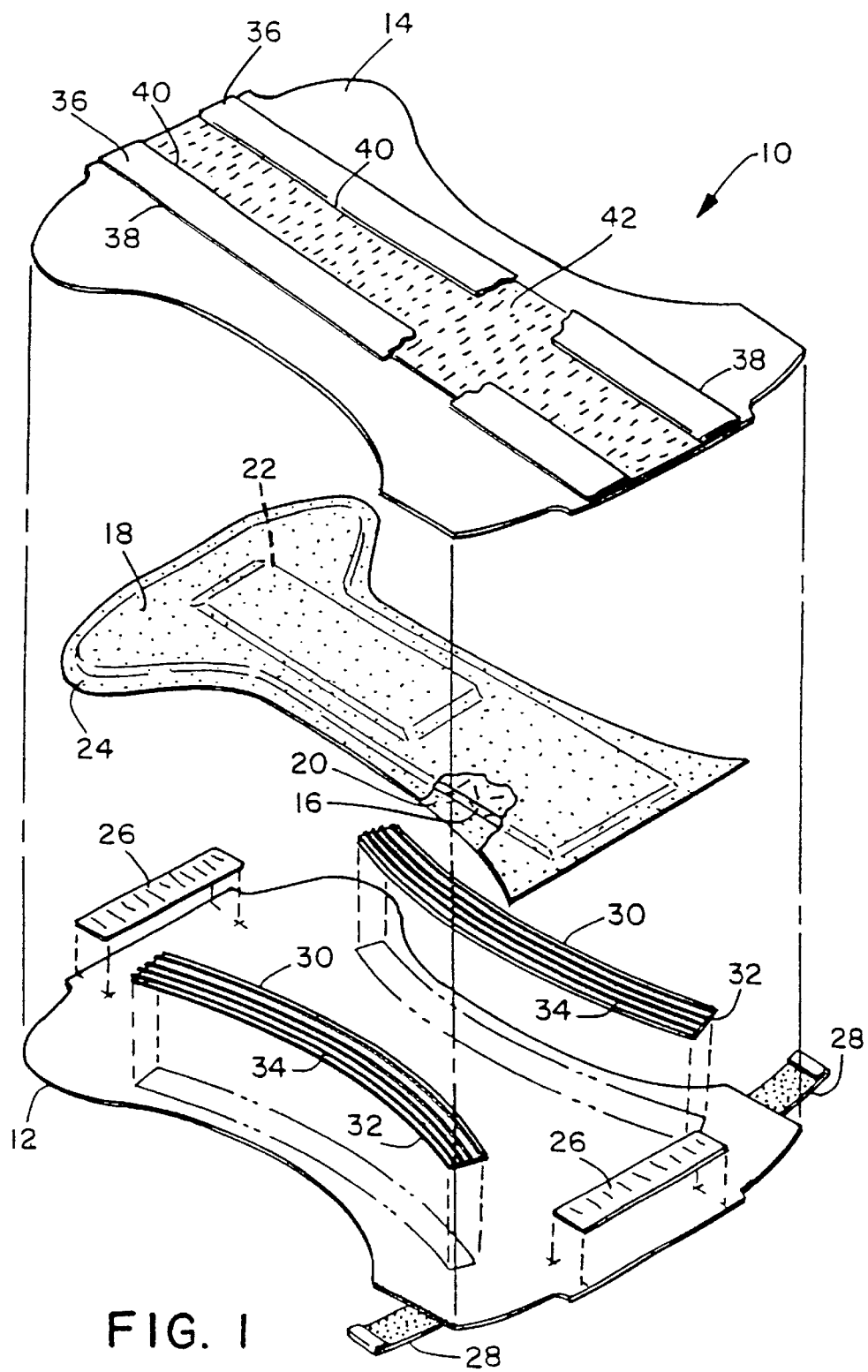
FIG. 1 is a partially cut-away exploded perspective view of one embodiment of a disposable diaper according to the present invention.

In one aspect, the present invention concerns absorbent composites and disposable absorbent garments possessing improved, desirable characteristics achieved by the careful selection and use of the superabsorbent material employed in forming such absorbent composites and disposable absorbent garments.

Specifically, in one aspect, the present invention concerns an absorbent composite comprising means for containing a superabsorbent material and a superabsorbent material contained by said containment means. In a second aspect the present invention concerns an absorbent composite comprising a mixture of fibers and a superabsorbent material. As used herein, the term "superabsorbent material" refers to a water-swellable, water-insoluble organic or inorganic material capable, under the most favorable conditions, of absorbing at least about 20 times its weight in an aqueous solution containing 0.9 weight percent of sodium chloride. It is preferable, but not essential, that the superabsorbent material be capable of absorbing at least about 30 times its weight in an aqueous solution containing 0.9 weight percent of sodium chloride.) Organic materials suitable for use as a superabsorbent material of the present invention can include natural materials such as agar, pectin, guar gum, and the like; as well as synthetic materials, such as synthetic hydrogel polymers. Such hydrogel polymers include, for example, alkali metal salts of polyacrylic acids, polyacrylamides, polyvinyl alcohol, ethylene maleic anhydride copolymers, polyvinyl ethers, hydroxypropylcellulose, polyvinylmorpholinone; and polymers and copolymers of vinyl sulfonic acid, polyacrylates, polyacrylamides, polyvinylpyrridine, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Crosslinking may, for example, be by irradiation or by covalent, ionic, van der Waals, or hydrogen bonding. The superabsorbent materials may be in any form suitable for use in absorbent composites including particles, fibers, flakes, spheres, and the like. In one preferred embodiment of the present invention, the superabsorbent material comprises particles of a hydrocolloid, preferably an ionic hydrocolloid.

While a wide variety of superabsorbent materials are known, the present invention relates, in one aspect, to the proper selection and use of superabsorbent materials to allow formation of improved absorbent composites and disposable absorbent garments.

U.S. Pat. No. 5,147,343 issued Sep. 15, 1992, to Kellenberger describes the importance of using a superabsorbent material exhibiting the ability to absorb liquid while the superabsorbent material is under an applied restraining force. The restraining force described in the claims of this reference is approximately 0.3 pound per square inch (about 21,000 dynes per square centimeter).

It has been discovered that the performance of a superabsorbent material in certain absorbent composites comprising from about 30 to about 100 weight percent of said superabsorbent material depends, at least in part, on the ability of the superabsorbent material to absorb a liquid under a variety of restraining forces. That is, it has been discovered that the performance of a superabsorbent material relates not only to the ability of the superabsorbent material to absorb a liquid while under a single given restraining force (for example, about 0.3 pound per square inch) but over a broader range of restraining forces (for example, 0.01–0.9 pound per square inch, 690–62,053 dynes per square centimeter). The ability of a superabsorbent material to absorb a liquid under a variety of different restraining pressures has, for the purposes of this application, been quantified as the Pressure Absorbency Index.

The Pressure Absorbency Index is the sum of the Absorbency Under Load values (described herein below) for a superabsorbent material determined under the following loads: 0.01 pound per square inch (690 dynes per square centimeter); 0.29 pound per square inch (19995 dynes per square centimeter); 0.57 pound per square inch (39300 dynes per square centimeter); and 0.90 pound per square inch (62053 dynes per square centimeter). That is, the Absorbency Under Load values for a given superabsorbent material are determined under the restraining forces set forth above according to the method set forth below in connection with the examples. The Absorbency Under Load values determined under the restraining loads set forth above are then totaled to produce the Pressure Absorbency Index.

Superabsorbent materials suitable for use in the present invention have a Pressure Absorbency Index of at least 100, generally of at least about 105, particularly of at least about 110, more particularly of at least about 115, even more particularly of at least about 120; and most particularly of at least about 140.

As used herein, the Absorbency Under Load value of a particular superabsorbent material refers to the amount, in grams, of an aqueous, solution of sodium chloride (0.9 weight percent sodium chloride) which 1 gram of superabsorbent material can absorb in 60 minutes while under a given restraining load.

Superabsorbent materials suitable for use in the present invention may also suitably have a 16-hour extractables level, determined as set forth below in connection with the examples, of less than about 13 weight percent, particularly of less than about 10 weight percent, more particularly of less than about 7 weight percent, and even more particularly of less than about 3 weight percent.

Superabsorbent materials suitable for use in the present invention may also. suitably have a Vortex Time, determined as set forth below in connection with the examples, of less than about 45 seconds, particularly of less than about 30 seconds, more particularly of less than about 20 seconds and-even more particularly of less than about 15 seconds.

It has been discovered that acceptable, improved performance of absorbent composites and absorbent garments can be achieved by selecting and using superabsorbent materials having a combination of one or more of the described properties. For example, a given level of acceptable performance may be achieved by employing a superabsorbent material having a Pressure Absorbency Index of about 110. Alternatively, acceptable performance may be achieved by employing superabsorbent materials having a Pressure Absorbency Index of 100 and a 16-hour extractables level of less than about 13 weight percent. Still further, acceptable performance may be achieved by employing superabsorbent materials having a Pressure Absorbency Index of 100 and a Vortex Time of less than about 45 seconds.

Specifically, it has been discovered that while superabsorbent materials having a Pressure Absorbency Index of at least about 110 are believed to be preferred, superabsorbent materials having a lower Pressure Absorbency Index can perform satisfactorily if they have a 6-hour extractables level of less than about 13 weight percent or a Vortex Time of less than about 45 seconds. That is, the superabsorbent material properties of fast absorption rate (Vortex Time) and low extractables can "compensate" for a Pressure Absorbency Index of less than about 110.

Exemplary of specific superabsorbent materials suitable for use in the present invention are polyacrylate materials obtained from Stockhausen, Incorporated under the designations T-5121, T-5209, and T-5149, as well as a polyacrylate material obtained from Hoechst Celanese Corporation under the designation S-271-1675-03, as well as polyacrylate materials obtained from Dow Chemical, USA under the designations AFA 35-150 and AFA 65-13.

In one preferred embodiment of the present invention, the superabsorbent material is in the form of particles which, in the unswollen state, have maximum cross-sectional diameters within the range of from about 50 microns to about 1,000 microns, preferably within the range of from about 100 microns to about 800 microns, as determined by sieve analysis according to American Society for Testing Materials (ASTM) Test Method D-1921. It is understood that the particles of superabsorbent material, falling within the ranges described above, may comprise solid particles, porous particles, or may be agglomerated particles comprising many smaller particles agglomerated into particles within the described size ranges.

In addition to the superabsorbent materials described above, the absorbent composites according to the present invention comprise means to contain the superabsorbent material. Any means capable of containing the described superabsorbent materials, which means is further capable of being located in a disposable absorbent garment, is suitable for use in the present invention. Many such containment means are known to those skilled in the art. For example, the containment means may comprise a fibrous matrix such as an airlaid or wet laid web of cellulosic fibers, a meltblown web of synthetic polymeric fibers, a spunbonded web of synthetic polymeric fibers, a coformed matrix comprising cellulosic fibers and fibers formed from a synthetic polymeric material, airlaid heat-fused webs of synthetic polymeric material, open-celled foams, and the like.

Alternatively, the containment means may comprise two layers of material which are joined together to form a pocket or compartment, more particulary a plurality of pockets, which pocket contains the superabsorbent material. In such a case, at least one of the layers of material should be water-pervious. The second layer of material may be water-pervious or water-impervious. The layers of material may be cloth-like wovens and nonwovens, closed or open-celled foams, perforated films, elastomeric materials, or may be fibrous webs of material. When the containment means comprises layers of material, the material should have a pore structure small enough or tortuous enough to contain the majority of the superabsorbent material. The containment means may also comprise a laminate of two layers of material between which the superabsorbent material is located and contained.

Further, the containment means may comprise a support structure, such as a polymeric film, on which the superabsorbent material is affixed. The superabsorbent material may be affixed to one or both sides of the support structure which may be water-pervious or water-impervious.

The superabsorbent material is present in the,containment means in an amount of from about 30 to about 100 weight percent, alternatively of from about 40 to about 100 weight percent, alternatively, of from about 50 to about 100 weight percent, alternatively of from about 60 to about 100 weight percent, alternatively of from about 70 to about 100 weight percent, alternatively of from about 80 to about 100 weight percent, and finally of from about 90 to about 100 weight. percent based on total weight of the containment means and the superabsorbent material.

In one specific embodiment of the present invention, the containment means comprises two layers of material which are joined to form a pocket adapted to contain the superabsorbent material. The two layers are suitably formed from any material capable of containing the superabsorbent material including woven and nonwoven materials such as airlaid or wet laid fibers, meltblown fibers, spunbonded fibers, coformed fibers, binder fibers (such as bicomponent fibers), and the like, and are joined to form a pocket by heat fusion, sonic bonding, adhesives (such as water-soluble or water-sensitive adhesives, latex adhesives, hot melt adhesives, or solvent-based adhesives) and the like. Clearly, a wide variety of materials may be employed to form the two layers and to join the two layers together to form the pocket. The superabsorbent material is present in said pocket in an amount of from about 30 to about 100 weight percent, alternatively of from about 40 to about 100 weight percent, alternatively, of from about 50 to about 100 weight percent, alternatively of from about 60 to about 100 weight percent, alternatively of from about 70 to about 100 weight percent, alternatively of from about 80 to about 100 weight percent, and finally of from about 90 to about 100 weight percent based on total weight of the superabsorbent material present in said pocket and the weight of the two layers forming the pocket. In addition to the superabsorbent material, the pocket may contain a fibrous material or other filler material that does not unacceptably affect the absorbent properties of the superabsorbent material.

In another specific embodiment, the containment means comprises a matrix of fibers. The superabsorbent material is mixed with the fibers of the matrix. The superabsorbent material is present in the mixture of fibers and superabsorbent material in an amount of from about 30 to about 70 weight percent, particularly of from about 40 to about 70 weight percent and more particularly of from about 50 to about 70 weight percent based on total mixture weight.

Any fibers capable of forming a containment means capable of containing a superabsorbent material and of forming a composite when in combination with the superabsorbent material are believed suitable for use in the present invention. It is often preferred that the fibers are hydrophilic. As used herein, a fiber will be considered to be "hydrophilic" when it possesses a contact angle of water in air of less than 90 degrees. For the purposes of this application, contact angle measurements are determined as set forth by Good and Stromberg in "Surface and Colloid Science" Vol. 11 (Plenum Press, 1979).

Fibers suitable for use in the present invention include cellulosic fibers such as wood pulp fluff, cotton, cotton linters, rayon, cellulose acetate, and the like, as well as synthetic polymeric fibers. The synthetic polymeric fibers may be formed from inherently hydrophilic polymeric materials or may be formed from inherently hydrophobic polymeric materials (water in air contact angle of greater than 90°), which fibers are then treated to render at least the outer surface of the fibers hydrophilic. For example, hydrophilic fibers may be formed from an intrinsically hydrophilic polymer such as a block copolymer of nylon, e.g., nylon-6, and a polyethylene oxide diamine. Such block copolymers are commercially available from Allied-Signal Inc. under the trade designation HYDROFIL. Alternatively, the fibers may be formed from an intrinsically hydrophobic polymer such as a polyolefin or polyester which has been surface modified to provide a generally nonfugitive hydrophilic surface. Such a surface modified polyethylene is commercially available from the Dow Chemical Company under the trade designation ASPUN wettable polyethylene.

When the hydrophilic fibers are formed by applying a hydrophilic surface treatment to a generally hydrophobic polymer, it is believed desirable to employ a generally non-fugitive surface treatment in order to obtain the desired performance standards. Absorbent structures employed in absorbent garments such as diapers are often subjected to multiple insults of urine. If the surface treatment is fugitive it may be washed off with the initial insult, thus, exposing the hydrophobic fiber surface. The hydrophobic fiber surface may impede the absorption performance of the absorbent structure. Of course, there are instances where hydrophobic fibers may be employed, depending, in part, on the fluid to be absorbed.

The synthetic polymeric fibers suitable for use in the present invention are suitably formed through a melt-extrusion process wherein fibers of a polymeric material are extruded and attenuated to produce fibers having a desired diameter. Alternatively, the fibers may be formed through a spinning process. Any fiber-producing process known to those skilled in the art is believed to be suitable for use in the present invention.

Fibers suitable for use in the present invention generally have a length of at least about 1 millimeter. The fibers may have a maximum length approaching infinity. That is to say, the fibers may be essentially continuous such as those fibers formed through a meltblowing process under certain conditions known to those skilled in the art.

Reference to a "mixture" is intended to refer to a combination of fibers and superabsorbent material in which the superabsorbent material is in direct contact with the fibers or is not substantially prevented from migrating into contact with the fibers. Thus, for example, in a multi-layered absorbent core in which the first layer comprises an airlaid mixture of wood pulp fluff and superabsorbent material and the second layer comprises only airlaid fluff, only the first layer is considered a "mixture" provided substantial dry migration of the superabsorbent material between the two layers is prevented. Methods of preventing such migration are known and include separating the layers by a tissue wrap sheet, high density fiber layer or similar means to prevent substantial dry migration of the superabsorbent material between the two layers. The mixture of superabsorbent material and fibers may be relatively homogenous or relatively non-homogenous. In the case of a non-homogenous mixture, the superabsorbent may be arranged in a gradient or may be layered with the fibers.

When the containment means comprises a mixture of fibers and a superabsorbent material, the mixture of fibers and superabsorbent material may be formed in a wide variety of ways. For example, the mixture may be formed by airlaying or wetlaying the fibers and superabsorbent material, according to processes known in the art, to form batts of the mixture. Airlaying the mixture of fibers and superabsorbent material is intended to encompass both the situation wherein preformed fibers are airlaid with the superabsorbent material as well as the situation in which the superabsorbent material is mixed with the fibers as the fibers are being formed, such as through a meltblowing process.

Because of the relatively high concentrations of superabsorbent material present in the absorbent composites of the present invention, the absorbent composites according to the present invention may have an average thickness of less than about 0.5 inch (12.7 millimeters), particularly of less than about 0.3 inch (7.6 millimeters), and more particularly of less than about 0.15 inch (3.8 millimeters).

As used herein, reference to the average thickness of an absorbent composite is intended to refer to the average of a number of thickness measurements taken under an applied load of about 0.2 pound per square inch. The number of thickness measurements taken is sufficient to represent the average thickness of the entire absorbent composite.

The absorbent composites of the present invention generally have an average basis weight of from about 50 to about 1000 grams per square meter, particularly of from about 100 to about 900 grams per square meter. The average basis weight of an absorbent composite can be determined by weighing the absorbent composite, determining the surface area of a major planar surface of the absorbent composite and converting to standard units such as grams per square meter.

The absorbent composites according to the present invention are suited to absorb many fluids including body fluids such as urine, menses, and blood, and are suited for use in absorbent garments such as diapers, adult incontinence products, bed pads, and the like; in catamenial devices such as sanitary napkins, tampons, and the like; and in other absorbent products such as wipes, bibs, wound dressings, food packaging, and the like. Accordingly, in another aspect, the present invention relates to a disposable absorbent garment comprising an absorbent composite as described above. A wide variety of absorbent garments are known to those skilled in the art. The absorbent composites of the present invention can be incorporated into such known absorbent garments. Exemplary absorbent garments are generally described in U.S. Pat. No. 4,710,1871 issued Dec. 1, 1987, to Boland et al.; U.S. Pat. No. 4,762,521 issued Aug. 9, 1988, to Roessler et al.; U.S. Pat. No. 4,770,656,issued Sep. 13, 1988, to Proxmire et al.; U.S. Pat. No. 4,798,603 issued Jan. 17, 1989, to Meyer et al.; and commonly assigned U.S. patent application Serial No. 07/757,760 filed Sep. 11, 1991, in the name of Hanson et al., now U.S. Pat. No. 5,509,915, issued Apr. 23, 1996 (EP 539,703); Ser. No. 08/145,924, filed Oct. 29, 1993, by Tanzer et al., now U.S. Pat. No. 5,411,497, issued May 2, 1995; Ser. No. 08/145,925 filed Oct. 29, 1993, by Tanzer et al., now U.S. Pat. No. 5,433,715, issued Jul. 18, 1995; Ser. No. 08/145,926, filed Oct. 29, 1993, by Tanzer et al., now (via application Ser. No. 08/369,558, filed Jan. 6, 1995) U.S. Pat. No. 5,593,399, issued Jan. 14, 1997; and Ser. No. 08/145,927, filed Oct. 29, 1993, by Tanzer et al., now U.S. Pat. No. 5,425,725, issued Jun. 20, 1995, which references are incorporated herein by reference.

As a general rule, the absorbent disposable garments according to the present invention comprise a body-side liner adapted to contact the skin of a wearer, an outer cover superposed in facing relation with said liner, and an absorbent composite, such as those described above, superposed on said outer cover and located between the body-side liner and the outer cover.

Those skilled in the art will recognize materials suitable for use as the body-side liner and outer cover. Examples of materials suitable for use as the body-side liner are hydrophilized spunbonded polypropylene or polyethylene having a basis weight of from about 15 to about 25 grams per square meter, and the like. Examples of materials suitable for use as the outer cover are water-impervious materials, such as polyolefin films, as well as water-pervious or water vapor-pervious materials.

Turning now to the drawings, FIG. 1 illustrates an exploded perspective view of a disposable diaper according to one embodiment of the present invention. Disposable diaper 10 includes an outer cover 12, a body-side liner 14, and an absorbent composite 16 located between the body-side liner 14 and the outer cover 12. The absorbent composite 16 comprises an airlaid mixture of wood pulp fibers and superabsorbent material. The absorbent composite is surrounded by a two-piece wrap sheet comprising upper wrap sheet layer 18 and lower wrap sheet layer 20. The absorbent composite 16 has a profiled thickness to define an area 22 of increased basis weight. The two-piece wrap sheet extends beyond the edges of the absorbent composite 16 to define perimeter 24 which can be sealed to prevent superabsorbent material from migrating out of the diaper.

Attached to outer cover 12 are waist elastics 26, fastening tapes 28 and leg elastics 30. The leg elastics 30 comprise a carrier sheet 32 and individual elastic strands 34.

The body-side liner 14 includes containment flaps 36 having proximal edges 38 and distal edges 40. A surge management layer 42 is located between the proximal edges 38 of the containment flaps 36.

The exact construction method and materials of the diaper illustrated in FIG. 1 is set forth in greater detail in commonly assigned U.S. patent application Ser. No. 07/757,760 filed Sep. 11, 1991, (now U.S. Pat. No. 5,509,915) in the name of Hanson et al., previously incorporated herein by reference. Possible modifications to the diaper illustrated in FIG. 1 are set forth in commonly assigned U.S. patent application Ser. No. 07/757,760 referenced above (now U.S. Pat. No. 5,509, 915) and in commonly assigned U.S. patent application Ser. No. 07/824,766 filed Jan. 17, 1992 in, now U.S. Pat. No. 5,364,382, issued Nov. 11, 1994, to Latimore et al. Such possible modifications include positioning the surge management layer 42 between the body-side liner 14 and the absorbent composite 16 and reducing the length of the surge management layer to extend the length of the absorbent composite or massing (reduce length and increase basis weight) the surge management layer in the area of the diaper where liquid waste initially accumulates (target zone).

Figure 2:
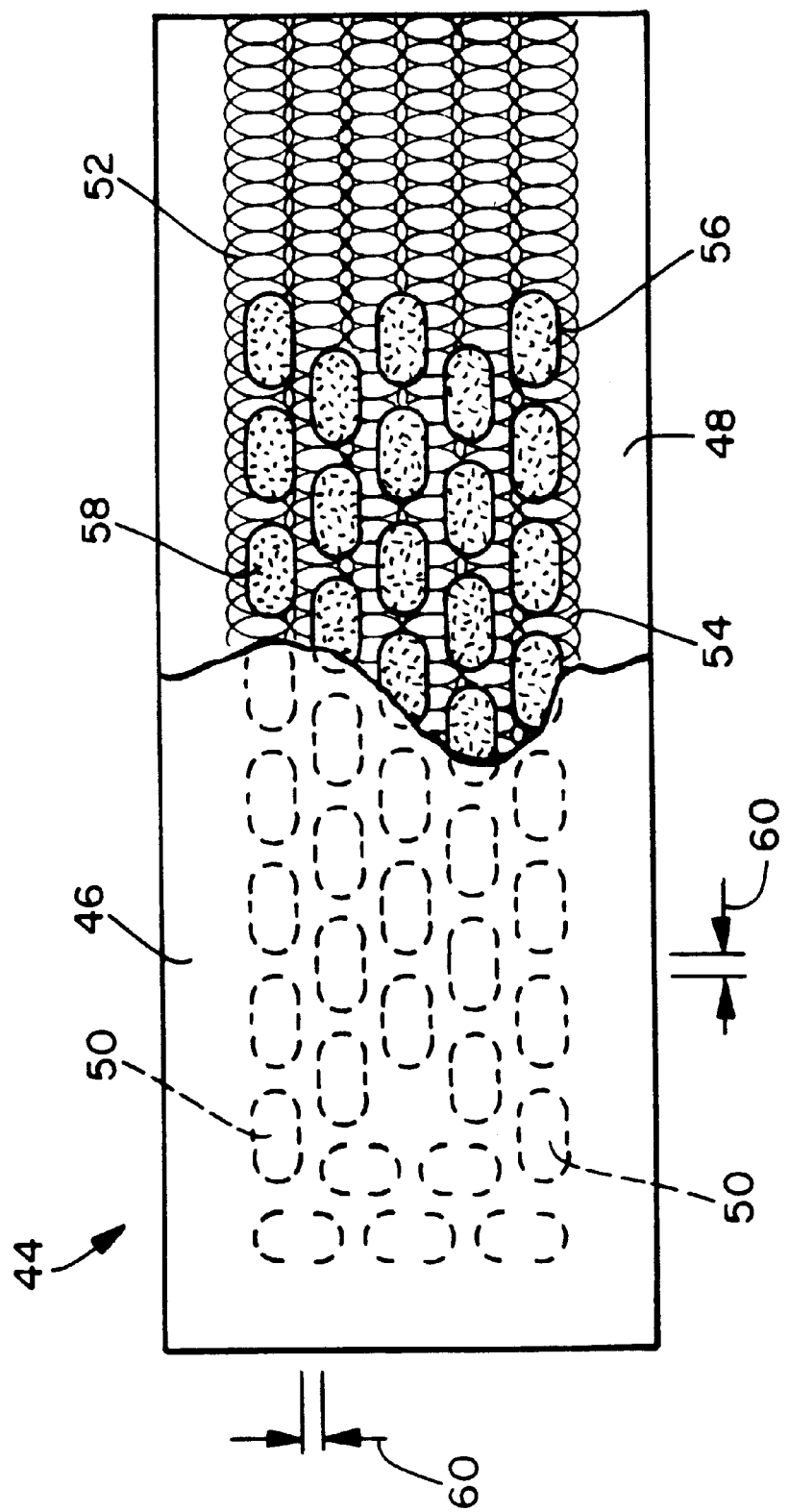
FIG. 2 is a partially cut-away plan view of an absorbent composite according to the present invention.

FIG. 2 illustrates an absorbent composite according to the present invention. With reference to FIG. 2, the absorbent composite 44 comprises a liquid permeable first layer 46, a second layer 48 and pockets 50 of superabsorbent material formed between the first layer 46 and second layer 48. The pockets 50 are defined by attachment means 52 which serve to operatively join the first and second layers. to form a laminate and to maintain the integrity of the laminate when the laminate is dry but to release when the laminate becomes wetted. Due to this release, the swelling of a superabsorbent material present in the pockets is not excessively restricted. Suitable attachment means include water sensitive adhesives, such as water soluble adhesives and embossing. The attachment means 52 secures together the first layer 46 and the second layer 48 to provide attached zones 54 and unattached zones 56. The unattached zones define pockets 50. A superabsorbent material 58 is located in the unattached zones 56 (and hence, in pockets 50). In addition to the superabsorbent material 58, the pockets 50 may contain a fibrous material such as cellulose fluff. Specifically, in one embodiment, the pockets may contain up to about 10 weight percent cellulose fluff based on the total weight of the superabsorbent material and the cellulose fluff. The pockets 50 are spaced by a distance 60. The spacing 60 is at least about 0.15 centimeter, alternatively at least about 0.25 centimeter or alternatively at least about 0.3 centimeter. Moreover, the pocket spacing 60 is suitably not more than about 3 centimeters, alternatively not more than about 1.9 centimeters, or alternatively not more than about 1.2 centimeters.

Figure 3:
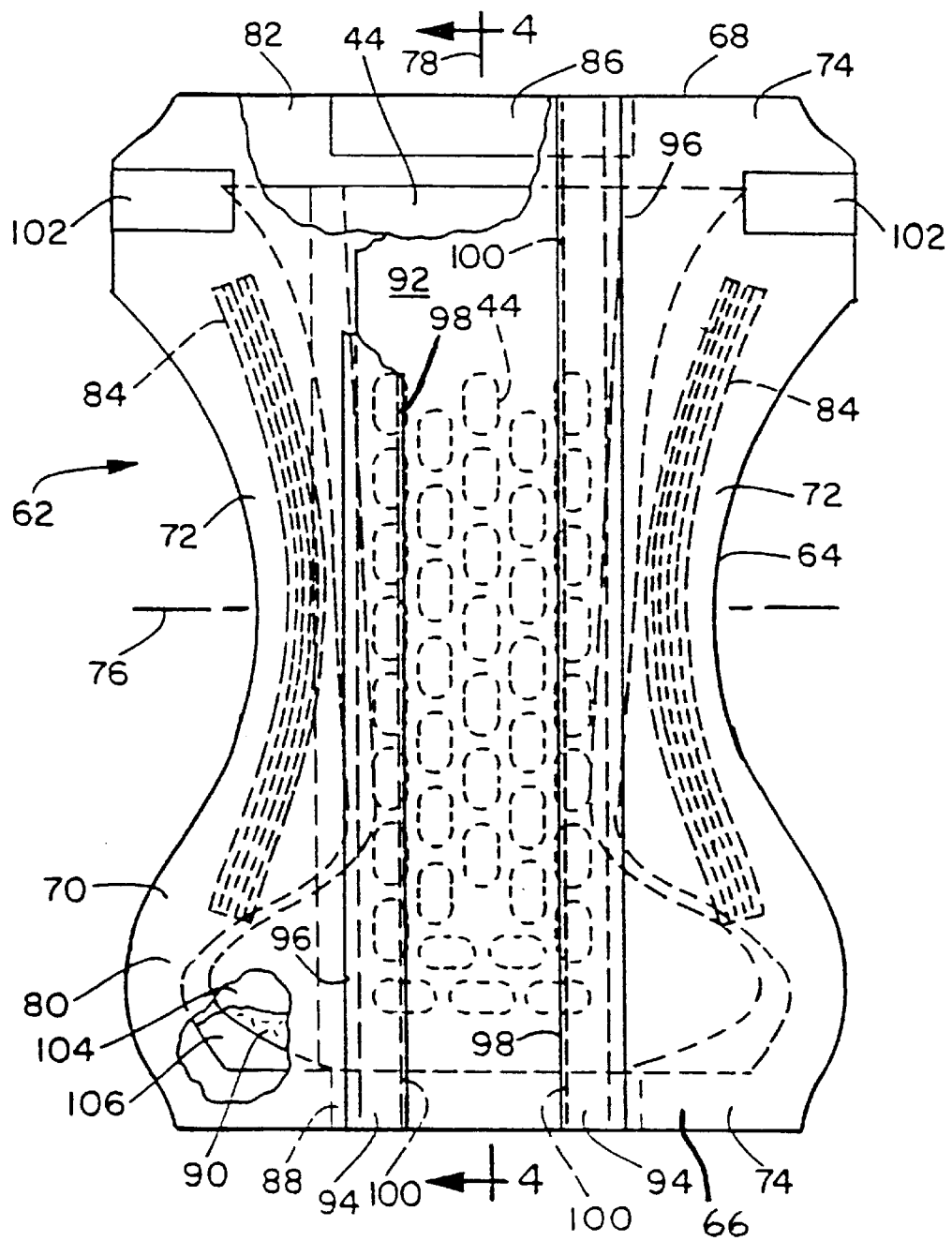
FIG. 3 is a partially cut-away plan view of a second embodiment of a disposable diaper according to the present invention.

FIG. 3 illustrates a disposable infant diaper incorporating the absorbent composite of FIG. 2. In FIG. 3, portions of the diaper are partially cut away to more clearly show the construction of the diaper 62. The side of the diaper which contacts the wearer is facing the viewer. The diaper 62 has a crotch region 64 which connects a front waistband region 66 and a rear waistband region 68. The outer edges of the diaper define a periphery 70 in which longitudinally extending side edge margins are designated 72 and laterally extending end edge margins are designated 74. In the illustrated embodiment, the side edges are curvilinear and contoured to define leg openings for the diaper. The end edges are shown as straight, but optionally may be curvilinear. The diaper additionally has a transverse centerline 76 and a longitudinal centerline 78. The diaper 62 can include a liquid permeable top sheet 80; a substantially liquid impermeable outer cover 82; an absorbent composite 44 positioned between the top sheet and the outer cover; leg elastic members 84; and waist elastic members 86 and 88. The top sheet 80, outer cover 82, absorbent composite 44, and elastic members 84, 86, and 88 may be assembled in a variety of well known diaper configurations.

Figure 4:
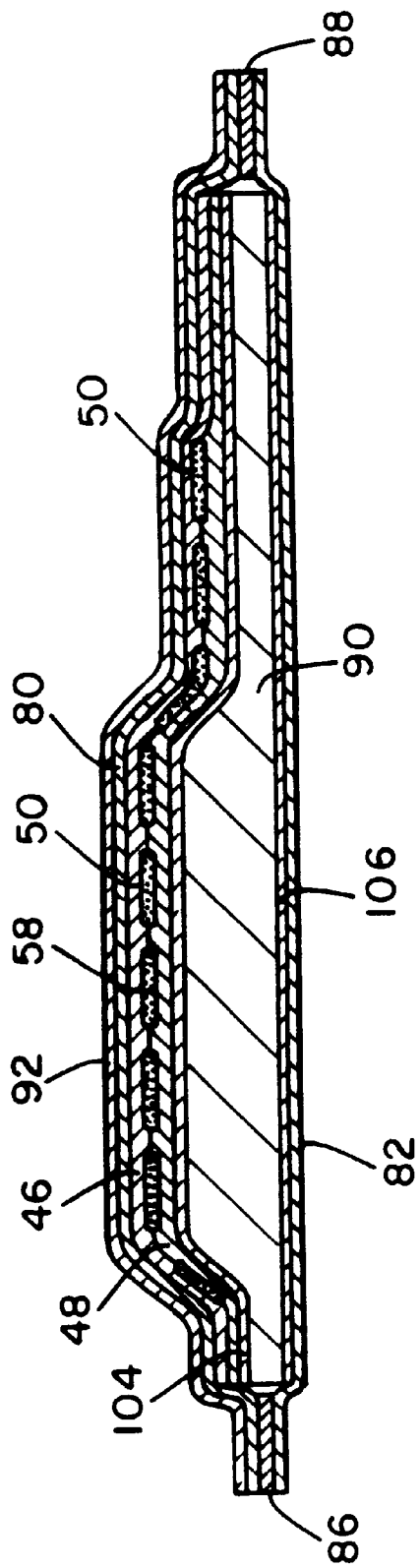
FIG. 4 is a cross-sectional view taken along line 4—4 of FIG. 3.

With reference to FIGS. 3 and 4, the details of the absorbent structure of diaper 62 can be appreciated. Diaper 62 comprises the absorbent composite 44 which is responsible for storing and holding absorbed liquids, such as urine. The diaper 62 may also include a supplemental absorbent, such as an outer side distribution layer 90. Distribution layer 90 suitably comprises a substantially unbonded mass of hydrophilic material, such as cellulosic fibers. The cellulosic fibers may, for example, be composed of wood pulp fluff, creped wadding, paper toweling, or the like. Distribution layer 90 can alternatively be provided by nonwoven webs comprising hydrophilic or hydrophilized fibers such as fibers composed of polyester, polypropylene, polyethylene, cotton, and the like. In the case of inherently hydrophobic fibers such as polyester or polypropylene fibers the hydrophobic fibers may be hydrophilized by means known in the art.

Diaper 62 further comprises a surge management portion 92 which is illustrated as being located on a body side surface of top sheet 80 or, alternatively, may be located on an outer side surface of the top sheet 80. The surge management portion 92 may be a layer composed of a meltblown or spunbonded web of polyolefin fibers. The surge management portion may also be a bonded-carded-web composed of natural and/or synthetic fibers. The surge management portion may be composed of a substantially hydrophobic material and the hydrophobic material may optionally be treated with a surfactant or otherwise processed to impart a desired level of wettability and hydrophilicity.

The diaper 62 further comprises containment flaps. In the illustrated arrangement, containment flaps 94 are attached to top sheet layer 80 along fixed (proximal) edges 96 of the flaps. A movable (distal) edge 98 of each containment flap includes a flap elastic member 100 comprising one or more individual strands of elastomeric material.

Fastening means, such as tape tab fasteners 102 are typically applied at the lateral, side ends of the rear waistband region 68 of diaper 62 to provide a mechanism for holding the diaper on the wearer in a conventional manner. The outer side distribution layer 90 is wrapped with a body side wrap sheet 104 and an outer side wrap sheet 106. Such wrap sheets typically comprise cellulosic fiber tissue or nonwoven layers such as a spunbond material.

This structure described in FIGS. 2–4 provides an absorbent composite which securely locates and contains the superabsorbent material in a selected array of pockets when the article is dry. When the article becomes wetted, the absorbent composite can maintain the location of the superabsorbent material while accommodating the increased volume of the swollen superabsorbent. Further, when the attachment means is water-sensitive, the water-sensitivity of the attachment means can help maintain interstitial channels between the individual pocket regions to facilitate the flow of liquid to each of the pocket regions. Accordingly, the quantity of superabsorbent material contained in the pocket regions of the absorbent composite can be more efficiently utilized, and the absorption characteristics of the composite can be improved. As a result, the diaper in which the absorbent composite is located can be configured with a thinner structure which is capable of absorbing larger amounts of liquid and exhibits reduced leakage. The thinner structure can in turn provide improved fit and comfort.

Materials suited for use in forming the diaper illustrated in FIGS. 2–4 are set forth in greater detail in commonly assigned U.S. patent application Ser. No. 07/757,760 filed Sep. 11, 1991, in the name of Hanson et al., previously incorporated herein by reference. Further, the exact construction method and materials of the diaper illustrated in FIGS. 2–4 are set forth in greater detail in commonly assigned U.S. patent application Ser. No. 08/145,924, filed Oct. 29, 1993, by Tanzer et al., now U.S. Pat. No. 5,411,497, issued May 2, 1995; Ser. No. 08/145,925, filed Oct. 29, 1993, by Tanzer et al., now U.S. Pat. No. 5,433,7151, issued Jul. 18, 1995; Ser. No. 08/145,926, filed Oct. 29, 1993, by Tanzer et al., now (via application Ser. No. 08/369,558, filed Jan. 6, 1995) U.S. Pat. No. 5,593,399, issued Jan. 14, 1997; and Ser. No. 08/145,927, filed Oct. 29, 1993, by Tanzer et al., now U.S. Pat. No. 5,425,725, issued Jun. 20, 1995, the teachings of which have earlier been incorporated herein by reference.

Test Methods

Absorbency Under Load (AUL)

Figure 5:
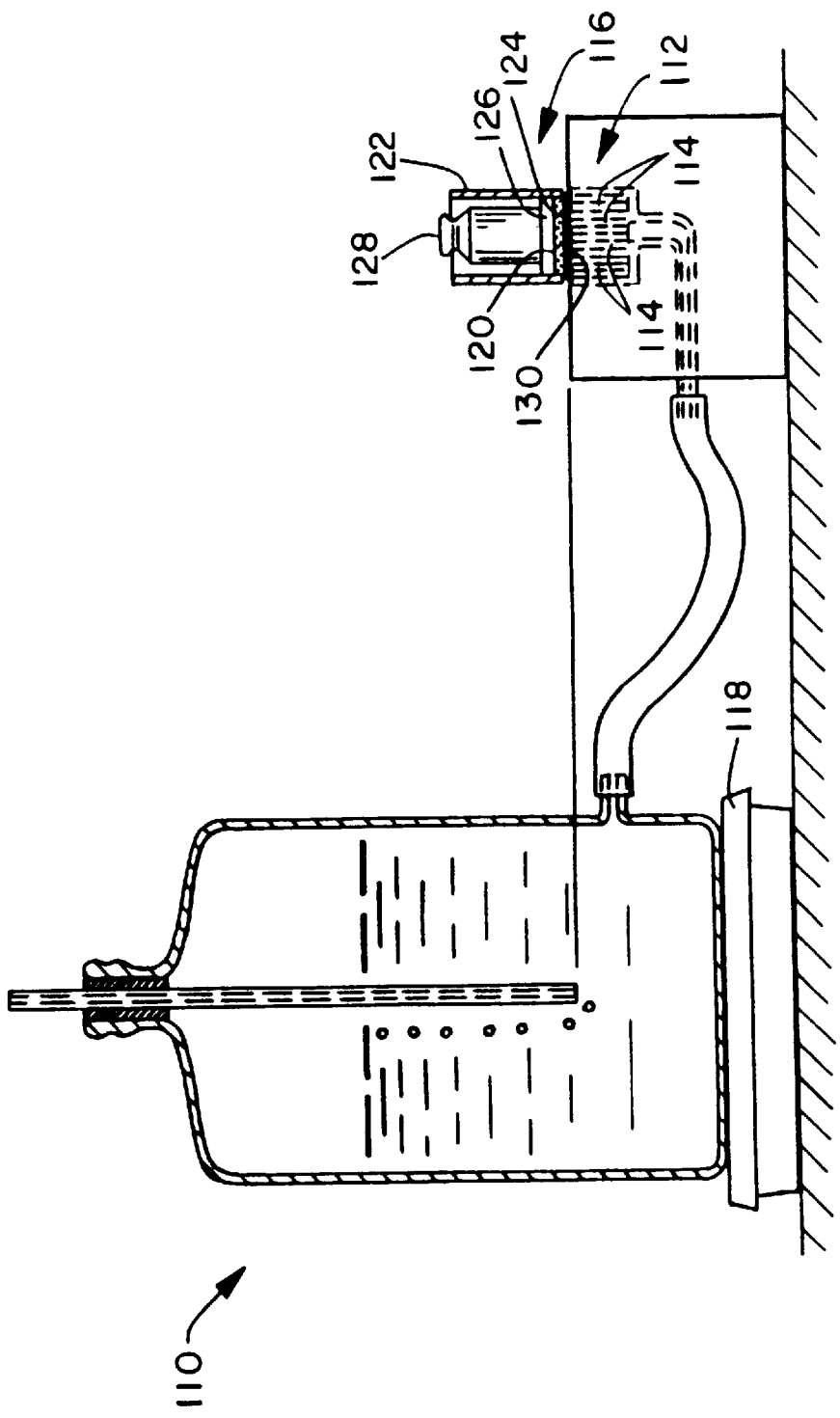
FIG. 5 is a partially cut-away illustration of equipment for determining the Absorbency Under Load (AUL) of superabsorbent material.

The ability of a superabsorbent material to absorb a liquid while under a load is determined as follows. With reference to FIG. 5, a Demand Absorbency Tester (DAT) 110 is used, which is similar to the GATS (Gravimetric Absorbency Test System), available from M/K Systems, Danners, Mass., as well as the system described by Lichstein at pages 129–142 of the INDA Technological Symposium Proceedings, March 1974. A porous plate 112 is used, having ports 114 confined within a 2.5 centimeter diameter area and covered by the Absorbency Under Load (AUL) apparatus 116. An electrobalance 118 is used to measure the flow of fluid into the superabsorbent particles 120. For this test, the fluid employed is an aqueous solution containing 0.9 weight percent sodium chloride used at room temperature (approximately 23° C.).

The special AUL apparatus 116 used to contain the superabsorbent particles comprises a cylinder 122 made from 1 inch (2.54 centimeters) inside diameter thermoplastic tubing which is machined-out slightly to be sure of concentricity. A 100 mesh stainless steel wire cloth 124 is adhered on the bottom of cylinder 122 by means of an adhesive. Alternatively, the stainless steel wire cloth 124 can be fused to the bottom of cylinder 122 by heating the wire cloth in a flame until red hot, after which the cylinder is, held onto the cloth until cooled. A soldering iron can be used to touch up the seal if unsuccessful or if it breaks. Care must be taken to maintain a flat, smooth bottom, and not distort the inside of the cylinder. A 4.4 gram piston 126 is made from 1 inch diameter solid material (e.g., PLEXIGLASS) and is machined to closely fit without binding in the cylinder 122. The piston 12 is used to provide the restraining load of 0.01 pound per square inch. A weight 128 is used to provide the greater degrees of restraining load. As discussed above, the greater restraining loads are 0.29 pound per square inch, 0.57 pound per square inch, and 0.90 pound per square inch. Accordingly, a 100, 200, and 317 gram weight is used to provide the respective restraining loads (in addition to the 4.4 gram piston 126). A sample of superabsorbent particles weighing 0.160 (±0.005) gram is utilized for testing AUL. The sample is taken from granules which are pre-screened through U.S. standard 30 mesh and retained on U.S. standard 50 mesh (300–600 microns). The particles, when tested, have a moisture content of less than about 5 weight percent.

This test is initiated by placing a 3 centimeter diameter GF/A glass filter paper 130 onto the plate 112. The paper is sized to be larger than the internal diameter and smaller than the outside diameter of the cylinder 122 to ensure good contact while eliminating evaporation over the ports 114 of the DAT 110 and then allowing saturation to occur. The particles 120 are weighed on weighing paper and placed on the wire cloth 124 at the bottom of the AUL apparatus 116. The apparatus 116 is shaken to level the particles 120 on the wire cloth 124. Care is taken to be sure no particles are clinging to the wall of the cylinder 122. After carefully placing, without pressing, the piston 126 and, optionally, weight 128 on the particles 120 in the cylinder 122, the AUL apparatus 116 is placed on the glass filter paper 130. The amount (in grams) of fluid picked up is monitored as a function of time either directly by hand, with a strip-chart recorder, or directly into a data acquisition or personal computer system.

The amount (in grams) of fluid picked up after 60 minutes, divided by the weight of the sample (0.160 gram) is the AUL value in grams of fluid picked up per gram of sample (g/g). The rate of fluid picked up can also be measured. Two checks can be made to ensure the accuracy of the instantaneous final readout. First, the height the piston 126 rises, multiplied by the cross-sectional area of the cylinder 122 should equal the volume of fluid picked up. Second, the AUL apparatus 116 can be weighed before and after the test, and the difference in weight should nearly equal the weight of fluid picked up. A minimum of three tests are performed on a given sample and averaged to assign an AUL value.

16-Hour Extractables Level

The following test methods are used to calculate the 16-hour extractable levels for the superabsorbent materials. The first test method is intended for use on carboxylic acid based superabsorbent materials. The second test method is intended for use with all other (noncarboxylic acid based) superabsorbent materials. It should be noted that both procedures may provide results that include the total amount of extractable material present in a particular superabsorbent material. The 16-hour extractables level is intended to refer only to those extractables which are polymeric in nature. Therefore, if a given superabsorbent material is known or believed to contain significant amounts of non-polymeric extractable material, such non-polymeric extractable material should be removed from the superabsorbent material in conventional fashion before performing the 16-hour extractables level test determination set forth below.

Method A (for Carboxylic Acid Based Superabsorbent Materials)

The test fluid employed in this test is an aqueous solution containing 0.9 weight percent of sodium chloride. In essence, the superabsorbent material is mixed with the saline solution for 16 hours. The superabsorbent material is then allowed to settle. A portion of the saline solution is filtered and an aliquot of the filtrate is taken. The pH of the filtrate is raised to 10. The filtrate is then titrated to a pH of 2.7 with acid. From the titration data, the amount of extractable carboxylic acid containing polymer can be determined. The exact test process is as follows.

1. 75 milliliters (±0.1 milliliter) of a 0.9 weight percent sodium chloride solution is added to a disposable beaker.
2. 0.4 gram (±0.01 gram) of a superabsorbent material to be tested is added to the sodium chloride solution. The superabsorbent material is pre-screened, as described above, to have a particle size of 300–600 microns.
3. The mixture is placed on a flat bed horizontal shaker (commercially available from Baxter Scientific under the trade designation LAB-LINE) at low speed and allowed to stand, with shaking, for 16 hours.
4. The mixture of superabsorbent material and sodium chloride solution is filtered through an 8 micron WHATMAN filter paper.
5. 20 grams (±0.01 gram) of the filtrate is placed in a disposable beaker. The beaker is configured such that a pH electrode can be adequately immersed in the filtrate and the filtrate is stirred. The instrument used for the titration is a Brinkmann Metrohm 672 Titroprocessor equipped with a Metrohm 655 Dosimat and a combination pH electrode. The instrumental parameters for a set end point titration are as follows:

| End Point 1 (pH) | 2.7 |
|---|---|
| dyn. delta pH 1 | 3.8 |
| drift | 1.0 mV/s |
| t (delay) 1 | 20 sec. |
| End Point 2 (pH) | off |
| Temp. | 25.0° C. |
| Stop Volume | 70.00 ml |

6. The pH of the filtrate is raised to 10 with a 0.1 normal sodium hydroxide solution. The solution is then back titrated with a standardized 0.1 normal hydrochloric acid solution to a pH of 2.7.
7. 20 milliliters of the 0.9 weight percent sodium chloride solution are subjected to the titration described above to serve as a solvent blank for each analysis.
8. The percent extractables is calculated according to the following formula:

$$\frac{(Vs - Vb) * N * MW * 75 * 100}{1000 * Ws * Wf} = \% \text{ extractables}$$

where
Vs=volume of HCl titrant needed to titrate filtrate
Vb=volume of HCl titrant needed to titrate the solvent blank
N=normality of HCl titrant
MW=gram equivalent weight of superabsorbent polymer (88.5 for 75% neutralized sodium poly(acrylic acid))
75=total volume of solution
Ws=weight of superabsorbent polymer (0.4 gram)
Wf=weight of filtrate (20.0 grams)

The percent extractables is expressed as a weight percent based on starting weight of the superabsorbent material.

Method B—Non-carboxylic Acid Based Superabsorbent Material

The extractables level for non-carboxylic acid based superabsorbent material is determined by a gravimetric procedure wherein the superabsorbent material samples are swollen for 16 hours in an aqueous solution containing 0.9 weight percent of sodium chloride. The polymer content in the filtrate is gravimetrically determined. The particular test procedure is as follows:

Into a 500 milliliter Erlenmeyer flask is weighed 0.25 gram (±0.1 milligram) of dry superabsorbent material. The superabsorbent material is pre-screened, as described above, to have a particle size of 300–600 microns. 250 milliliters of the 0.9 weight percent sodium chloride solution are added to the flask and the mixture is slowly stirred for 1 hour. After 1 hour, stirring is stopped and the mixture is allowed to stand for 15 hours. At the end of the 15 hour period, enough supernatant is filtered through an eight micron WHATMAN filter paper to obtain at least 40 milliliters of filtrate. Exactly 40 milliliters of the filtrate is placed into a clean 100 milliliter round-bottomed flask, and the solution is concentrated on a rotary evaporator (water aspirator vacuum, bath temperature 55° C.). The remaining 2–3 milliliters of solution is quantitatively transferred to a tared weighing vial with the aid of additional distilled water. The solution in the weighing vial is reduced to dryness in an oven at 120° C. The vial is cooled, reweighed, and the weight of residue ($W_r$) is determined using the tare weight of the vial. The weight percent of the sodium chloride ($W_{NaCl}$) present in the 40 milliliters of filtrate is calculated. The weight percent of extractable polymer is calculated from the weight of dry polymer ($W_p$) and weight of residue ($W_r$) (corrected for the weight of the sodium chloride ($W_{NaCl}$)) according to the following equation:

$$\frac{(W_r - W_{NaCl}) * 250}{W_p * 40 * 100} = \% \text{ extractables}$$

wherein:
$W_r$=weight of residue
$W_{NaCl}$=weight of sodium chloride present in 40 ml. aliquot (0.009 times 40)
$W_p$=weight of dry polymer Vortex Time General Description The vortex test measures the amount of time in seconds required for 2 grams of a superabsorbent material to close a vortex created by stirring 50 milliliters of saline solution at 600 revolutions per minute on a magnetic stir plate. The time it takes for the vortex to close is an indication of the free swell absorbing rate of the superabsorbent material.

Equipment & Materials

1. Beaker, 100 milliliters
2. Programmable magnetic stir plate, capable of providing 600 revolutions per minute (such as that commercially avail able from PMC Industries, under the trade designation DATAPLATE Model #721).
3. Magnetic stir bar without rings, 7.9 millimeters×32 millimeters, TEFLON covered (such as that commercially available from Baxter Diagnostics, under the trade designation S/P brand single pack round stirring bars with removable pivot ring).
4. Stopwatch
5. Balance, accurate to +/−0.01 gram
6. Saline solution, 0.87 w/w percent, Blood Bank Saline available from Baxter Diagnostics (considered, for the purposes of this application to be the equivalent of 0.9 weight percent saline
7. Weighing paper
8. Room with standard condition atmosphere: Temperature=23° C. +/−1 degree C. and Relative Humidity=50 percent +/−2 percent Test Procedure 1. Measure 50 grams +/−0.01 gram of saline solution into the 100 milliliter beaker.
2. Place the magnetic stir bar into the beaker.
3. Program the magnetic stir plate to 600 revolutions per minute.
4. Place the beaker on the center of the magnetic stir plate such that the magnetic stir bar is activated. The bottom of the vortex should be near the top of the stir bar.
5. Weigh out 2 grams +/−0.01 gram of the superabsorbent material to be tested on weighing paper.

NOTE: The superabsorbent material is tested as received (i.e. as it would go into an absorbent composite such as those described herein). No screening to a specific particle size is done, though the particle size is known to have an effect on this test.

6. While the saline solution is being stirred, quickly pour the superabsorbent material to be tested into the saline solution and start the stopwatch. The superabsorbent material to be tested should be added to the saline solution between the center of the vortex and the side of the beaker.
7. Stop the stopwatch when the surface of the saline solution becomes flat and record the time.
8. The time, recorded in seconds, is reported as the Vortex Time.

EXAMPLES

Example 1

Superabsorbent materials were obtained from Stockhausen, Inc., Greensboro, N.C.; Dow Chemical Company, Midland, Mich.; and Hoechst Celanese Corporation, Portsmouth, Va. All of the superabsorbent materials were based on acrylic acid and all were sodium salts (Na salt). The supplier of the superabsorbent material, designation under which it was received, and general composition of the superabsorbent material are set forth in Table 1 which follows:

TABLE 1

| Sample | Designation | Supplier | Composition |
|---|---|---|---|
| A | T-5121-1 | Stockhausen, Inc. | PVA/PAA[1] - Na Salt |
| B | T-5121-2 | Stockhausen, Inc. | PVA/PAA - Na Salt |
| C | T-5121-3[2] | Stockhausen, Inc. | PVA/PAA - Na Salt |
| D | T-5121-4[3] | Stockhausen, Inc. | PVA/PAA - Na Salt |
| E | T-5121-5[4] | Stockhausen, Inc. | PVA/PAA - Na Salt |
| F | Favor 835 | Stockhausen, Inc. | PVA/PAA - Na Salt |
| G | W45926-3 | Stockhausen, Inc. | PVA/PAA - Na Salt |
| H | T-5149 | Stockhausen, Inc. | PVA/PAA - Na Salt |
| I | T-5209 | Stockhausen, Inc. | PVA/PAA - Na Salt |
| J | AFA 10-10 | Dow Chemical | PAA[5] - Na Salt |
| K | AFA 5-54 | Dow Chemical | PAA/PAA - Na Salt |
| L | AFA 5-97 | Dow Chemical | PAA - Na Salt |
| M | AFA 5-102 | Dow Chemical | PAA - Na Salt |
| N | AFA 35-150 | Dow Chemical | PAA - Na Salt |
| O | AFA 5-31 | Dow Chemical | PAA/PAA - Na Salt |
| P | S-271-1675-03 | Hoechst Celanese | Starch/PAA[6] - Na Salt |
| Q | IM 3900 | Hoechst Celanese | Starch/PAA - Na Salt |
| R[7] | IM 3900 | Hoechst Celanese[8] | Starch/PAA - Na Salt |
| S | P 8965 | Stockhausen, Inc. | PVA/PAA - Na Salt |

[1]PVA/PAA = crosslinked polyvinyl alcohol graft poly (acrylic acid)
[2]Also Favor SAB 870, Lot #9212414 Bag #10
[3]Also Favor SAB 870, Lot #9212414 Bag #5
[4]Also Favor SAB 870, Lot #9212484 Bag #21
[5]PAA = crosslinked poly (acrylic acid)
[6]Starch/PAA = crosslinked starch graft poly (acrylic acid)
[7]Heat treated at 210° C. for 30 minutes in a large dryer
[8]Supplier of base superabsorbent material, heat treated after purchase.

The superabsorbent materials described in Table 1 were subjected to testing to determine their Absorbency Under Load values under a variety of restraining loads, their Pressure Absorbency Index, and their 16-hour extractables level. The results of this testing are set forth in Table 2. Unless otherwise indicated, all Absorbency Under Load data points represent the average of three test values. All 16-hour extractable values represent a single test value or the average of two test values.

TABLE 2

| | Absorbency Under Load | | | | | |
|---|---|---|---|---|---|---|
| Sample | 0.01 psi | 0.29 psi | 0.57 psi | 0.9 psi | PAI[1] | Extract[2] |
| A | 42.6 | 30.4 | 24.3 | 20.1 | 117.3 | 4.8 |
| B | 44.4 | 31.6 | 25.0 | 17.4 | 118.4 | 7.0 |
| C | 48.1 | 33.3 | 25.8 | 13.5 | 120.7 | 6.4 |
| D | 46.3 | 33.2 | 26.4 | 15.0 | 120.9 | 6.2 |
| E | 46.5 | 32.4 | 26.3 | 18.3 | 123.5 | 6.4 |
| F | 39.9 | 26.3 | 10.8 | 8.3 | 85.3 | 5.1 |
| G | 44.5 | 31.9 | 19.8 | 11.0* | 107.2 | 6.6 |
| H | 42.0 | 30.7 | 24.8 | 16.5** | 114.0 | 4.9 |
| I | 42.7 | 30.8 | 25.4 | 21.2 | 120.1 | 6.5 |
| J | 43.3 | 28.9 | 12.5 | 6.9 | 91.6 | 2.6 |
| K | 40.8 | 26.6 | 17.3 | 10.5 | 95.2 | 5.5 |
| L | 42.7 | 29.7 | 24.8 | 15.8 | 113.0 | 6.5 |
| M | 46.3 | 29.7 | 20.3 | 10.9 | 107.2 | 9.5 |
| N | 40.9 | 29.4 | 25.6 | 20.5 | 116.4 | 3.7 |
| O | 42.4 | 29.8 | 15.5 | 9.4 | 97.1 | 5.4 |
| P | 47.3 | 33.0* | 23.3* | 11.5* | 115.1 | 2.7 |
| Q | 41.2 | 28.3 | 14.2 | 8.6 | 92.3 | 2.2 |

TABLE 2-continued

| | Absorbency Under Load | | | | | |
|---|---|---|---|---|---|---|
| Sample | 0.01 psi | 0.29 psi | 0.57 psi | 0.9 psi | PAI[1] | Extract[2] |
| R | 38.6 | 28.4* | 23.9 | 13.5 | 104.4 | 3.2 |
| S | 51.4 | 33.9 | 20.4 | 11.5 | 117.2 | 14.7 |

[1]Pressure Absorbency Index
[2]16-hour extractables (weight percent)
*Average of 6 test values instead of 3
**Average of 9 test values instead of 3

A number of the superabsorbent materials described above in Tables 1 and 2 were incorporated into disposable diapers generally having the construction set forth in commonly assigned U.S. patent application Ser. No. 07/7 57,7, 60 filed Sep. 11, 1991, in the name of Hanson et al (now U.S. Pat. No. 5,509,915). More specifically, the diapers employed in the use test were of the same general configuration as those diapers commercially (available from the Kimberly-Clark Corporation under the trade designation HUGGIES UltraTrim Step 3. The UltraTrim diapers comprised an absorbent core consisting of a mixture of wood pulp fibers and superabsorbent material surrounded by a two-piece wrap sheet. The diapers employed in the use test were identical to the commercial UltraTrim diapers with the exception that the superabsorbent materials described above were employed as the superabsorbent material and that the density and basis weight of the mixture of superabsorbent material and wood pulp fibers varied slightly from use test to use test and was slightly different than that in the commercial UltraTrim product.

In essence, the HUGGIES UltraTrim Step 3 diapers comprised a 1.25 mil thick back sheet composed of polyethylene film and an absorbent pad. The absorbent pad included from about 11 to about 14 grams of wood pulp fibers and from about 10 to about 12 grams of a superabsorbent material selected from those described above. The fibers and superabsorbent material were arranged to provide a total, average basis weight of from about 475 to about 540 grams per square meter and a density of from about 0.21 to about 0.32 grams per cubic centimeter. The absorbent pad also included a wet-strength cellulosic tissue which was placed about the mass of wood pulp fibers and superabsorbent material. The tissue wrap had a weight of about 2.3 grams and a basis weight of about 16–21 grams per square meter. The resultant absorbent pad was sandwiched between the back sheet and a top sheet composed of a spunbond web of polypropylene fibers. The top sheet material was sized to be substantially coextensive with the diaper back sheet and was composed of polypropylene fibers having a fiber denier within the range of from about 2.8–3.2 denier. The fibers formed a nonwoven spunbonded web having a basis weight of about 22 grams per square meter and a web density of about 0.10 gram per cubic centimeter. A surge management layer, composed of a bonded carded web, was attached to the body-side surface of the top sheet with a pattern of hot melt adhesive. The surge management material had a width of about 4 inches and extended along the entire length of the diaper. The diaper further comprised containment flaps, leg elastics, elastic waistbands, and the like as set forth in U.S. patent application Ser. No. 07/757,760 (now U.S. Pat. No. 5,509,915). The surge management layer employed in the use test was a bonded-carded-web nonwoven fabric which included bicomponent fibers. The fabric had an overall basis weight of about 50 grams per square meter and an overall composite density of about 0.03 gram per cubic centimeter. The 2-layer composite comprised a first body-side layer which was a 15 gram per square meter layer composed of 100 percent polyethylene/polyester (PE/PET), sheath-core bicomponent fibers which had a fiber denier of about 1.8–3 denier. The second, outward side layer of the composite was composed of a 35 grams per square meter layer composed of a mixture of bicomponent fibers and single component fibers. The bicomponent fibers formed about 40 weight percent of the outward side layer. More particularly, 35 weight percent of the outward side layer was composed of 1.5 denier polyethylene/polypropylene (PE/PP) sheath core fibers with a flat crimp and 5 weight percent off the outward side layer was composed of 2 denier PE/PP sheath core fibers with a helical crimp. The single component fibers formed about 60 weight percent of the outward side layer and are 6 denies polyester fibers configured with a flat crimp. The specific absorbent core design features of the diapers employed in various use tests are set forth in Table 3 along with the results of the use tests.

The use test was conducted in the following manner. One hundred babies (50 male and 50 female) were recruited. The care giver for each child was given 10 diapers containing each superabsorbent material being evaluated in the use test. That is, the care giver was given 10 diapers of each code being evaluated in the use test. The care givers were instructed to use the 10 diapers from each code over 2 days under normal conditions and to indicate whether or not each diaper leaked. Diapers containing bowel movements were excluded from consideration when evaluating the data. A total of 1,000 diapers were used for each superabsorbent material sample.

The performance evaluation for the various samples was based on the leakage of the test diaper relative to a control diaper in the same use test. Because use tests conducted at different times with different babies will often yield different absolute leakage numbers, relative results within a given use test, as compared to a control, are a more representative indicator of the effectiveness of the superabsorbent being tested. Comparison between use tests can be highly variable. The control superabsorbent material for each of the use tests was sample Q.

The results of the diaper leakage testing are presented below in Table 3. The data in Table 3 is broken into 5 separate use tests and reports the percent overall leaks (% overall leaks) which is the total number of diapers with reported leakage divided by the total number of diapers (always excluding those diapers containing a bowel movement). The percent leakage between 0 and 300 milliliters (% 300 ml leaks) is determined by eliminating diapers containing bowel movements and urine loadings greater than 300 milliliters. For the purpose of evaluating the amount of fluid present in a diaper, 1 milliliter is assumed equal to 1 gram and the loadings are determined by weighing the used diapers and comparing to the average diaper weight for a given diaper configuration. The 0–300 milliliter leakage data reported is calculated by dividing the number of the remaining diapers which leaked by the number of remaining diapers. Finally, the diapers were categorized into diapers containing between 0 and 90 milliliters of urine, diapers containing between 91 and 180 milliliters of urine, and diapers containing between 181 and 270 milliliters of urine. The reported leakage data within each category (%90 ml leaks, %180 ml leaks, %270 ml leaks) is calculated by determining the number of diapers within each category which leaked and dividing it by the total number of diapers in each category.

TABLE 3

| Diaper | Superabsorbent[1] | Wt SAM[2] | Wt Fiber[3] | Density[4] | B.W.[5] | % Overall Leaks | % 300 ml Leaks | % 90 ml Leaks | % 180 ml Leaks | % 270 ml Leak |
|---|---|---|---|---|---|---|---|---|---|---|
| Use Test 1 | | | | | | | | | | |
| 1* | Q | 10 | 11.6 | 0.21 | 475 | 14.0 | 13.5 | 4.5 | 13.7 | 33.8 |
| 2 | A | 10 | 11.6 | 0.21 | 475 | 12.2 | 10.6 | 2.2 | 12.8 | 30.1 |
| 3 | O | 10 | 11.6 | 0.21 | 475 | 10.8 | 9.7 | 2.9 | 10.3 | 24.0 |
| 4 | R | 10 | 11.6 | 0.21 | 475 | 11.0 | 10.5 | 4.4 | 11.4 | 27.0 |
| Use Test 2 | | | | | | | | | | |
| 1* | Q | 12 | 11.6 | 0.28 | 520 | 9.0 | 9.1 | 2.1 | 10.2 | 28.1 |
| 2 | A | 12 | 11.6 | 0.28 | 520 | 8.4 | 6.3 | 3.6 | 5.6 | 18.9 |
| 3 | H | 12 | 11.6 | 0.28 | 520 | 7.4 | 6.7 | 2.0 | 4.9 | 31.1 |
| 4* | K | 12 | 11.6 | 0.28 | 520 | 10.4 | 10.5 | 5.1 | 10.1 | 27.1 |
| 5 | G | 12 | 11.6 | 0.28 | 520 | 10.5 | 9.5 | 4.6 | 12.1 | 21.1 |
| Use Test 3 | | | | | | | | | | |
| 1* | Q | 11 | 13.6 | 0.32 | 540 | 8.3 | 7.5 | 1.2 | 6.8 | 25.0 |
| 2 | B | 11 | 13.6 | 0.32 | 540 | 11.4 | 9.6 | 0.8 | 10.6 | 33.3 |
| 3 | H | 11 | 13.6 | 0.32 | 540 | 9.8 | 8.7 | 2.3 | 7.8 | 27.9 |
| Use Test 4 | | | | | | | | | | |
| 1* | Q | 11 | 13.6 | 0.23 | 540 | 14.8 | 13.4 | 8.7 | 9.0 | 31.3 |
| 2 | D | 11 | 13.6 | 0.23 | 540 | 15.0 | 14.0 | 7.7 | 11.9 | 30.4 |
| 3 | C | 11 | 13.6 | 0.23 | 540 | 15.5 | 12.9 | 9.1 | 13.2 | 25.3 |
| 4 | E | 11 | 13.6 | 0.23 | 540 | 14.8 | 13.9 | 8.2 | 12.6 | 27.4 |
| 5 | P | 11 | 13.6 | 0.23 | 540 | 12.6 | 11.2 | 7.5 | 11.4 | 21.5 |
| 6* | Q | 12 | 11.6 | 0.23 | 520 | 11.4 | 10.3 | 8.0 | 10.8 | 16.2 |
| 7 | D | 12 | 11.6 | 0.23 | 520 | 15.5 | 14.5 | 7.4 | 9.6 | 35.4 |
| Use Test 5 | | | | | | | | | | |
| 1* | Q | 12 | 11.6 | — | 520 | 11.6 | 9.8 | 3.7 | 7.7 | 27.1 |
| 2 | S | 12 | 11.6 | — | 520 | 11.5 | 10.0 | 1.7 | 9.1 | 33.3 |

[1]Superabsorbent used, selected from Table 1
[2]Grams of superabsorbent material used in the absorbent composite
[3]Grams of wood pulp fiber used in the absorbent composite
[4]Density of the absorbent composite in grams per cubic centimeter
[5]Basis weight of absorbent composite in grams per square meter
*Not an example of the present invention As can be seen from reference to Table 3, use tests 1 and 2 generally indicate that the absorbent composites according to the present invention generally perform better than absorbent composites employing superabsorbent materials outside of the present invention. It is believed that the best indication of performance is given by the percent overall leaks, the percent 300 milliliter leaks and the percent 180 milliliter leaks. The percent 180 milliliter leaks is believed to correlate to the diaper receiving a second insult of urine. Thus, while absorbent composites outside of the scope of the present invention may be able to perform well with less than a 90 milliliter load (one insult) they are generally less able to handle a second insult than the absorbent composites of the present invention.

Use test 3 does not show good correlation between performance and use of the absorbent composites of the present invention. It is believe this is due to the relatively high density of the absorbent composites (0.32 g/cc). Similarly, use test 4 does not shod good correlation.

It is believed that the importance of using a superabsorbent material with the PAI values set forth herein becomes more important as the concentration of the superabsorbent material in the absorbent composites increase. This appears to be demonstrated by the fact that use test 2 shows relatively good correlation between PIA and performance and employs superabsorbent composites containing about 51 weight percent of superabsorbent material. Those use tests showing less correlation between PAI and performance generally employ absorbent composites containing about 45–46 weight percent superabsorbent material.

Example 2

Superabsorbent materials were obtained from Stockhausen, Inc., Greensboro, N.C.; Dow Chemical Company, Midland, Mich.; and Hoechst Celanese Corporation, Portsmouth, Va. All of the superabsorbent materials were based on acrylic acid and all were sodium salts (Na salt). The supplier of the superabsorbent material, designation under which it was received, and general composition of the superabsorbent material are set forth in Table 4 which follows:

TABLE 4

| Sample | Designation | Supplier | Composition |
|---|---|---|---|
| A1 | IM3900[1] | Hoechst Celanese | Starch/PAA[2] - Na Salt |
| B1[3] | T 5209 | Stockhausen, Inc. | PVA/PAA[4] - Na Salt |
| C1[5] | S-271-1675-03 | Hoechst Celanese | Starch/PAA - Na Salt |
| D1 | AFA 5-44-1 | Dow Chemical | PAA - Na Salt |
| E1[6] | AFA 10-10 | Dow Chemical | PAA[7] - Na Salt |
| F1 | Favor 870[8] | Stockhausen, Inc. | PVA/PAA - Na Salt |
| G1 | AFA-65-13 | Dow Chemical | PAA - Na Salt |
| H1 | AFA-65-7-1 | Dow Chemical | PAA - Na Salt |
| I1 | AFA-65-7-2 | Dow Chemical | PAA - Na Salt |
| J1 | AFA-5-105-1 | Dow Chemical | PAA - Na Salt |
| K1 | AFA-5-105-2 | Dow Chemical | PAA - Na Salt |

TABLE 4-continued

| Sample | Designation | Supplier | Composition |
|---|---|---|---|
| L1 | AFA-65-9 | Dow Chemical | PAA - Na Salt |
| M1 | AFA-5-9-2 | Dow Chemical | PAA - Na Salt |

[1]Different lot number than sample Q from Table 1
[2]Starch/PAA = Crosslinked starch graft poly (acrylic acid)
[3]Same as Sample I from Table 1
[4]PVA/PAA = Crosslinked polyvinyl alcohol graft poly (acrylic acid)
[5]Same as Sample P from Table 1
[6]Same as Sample J from Table 1
[7]PAA = Crosslinked poly (acrylic acid)
[8]Lot Number 9212416

The superabsorbent materials described in Table 4 were subjected to testing to determine their Absorbency Under Load values under a variety of restraining loads, their Pressure Absorbency Index, and their Vortex Time. The results of this testing are set forth in Table 5. Unless otherwise indicated, all Absorbency Under Load data points represent the average of 3 test values. All Vortex Time values represent the average of three or four test values.

TABLE 5

| Sample | Absorbency Under Load | | | | PAI[1] | Vortex[2] |
|---|---|---|---|---|---|---|
| | 0.01 psi | 0.29 psi | 0.57 psi | 0.9 psi | | |
| A1 | 41.2 | 28.3 | 12.0 | 7.4 | 88.9 | 71 |
| B1 | 42.7 | 30.8 | 25.4 | 21.2 | 120.1 | 61 |
| C1 | 47.3 | 33.0* | 23.3* | 11.5* | 115.1 | 60 |
| D1 | 32.4 | 27.0 | 20.1 | 12.4 | 91.9 | 136 |
| E1 | 43.3 | 28.9 | 12.5 | 6.9 | 91.6 | 14 |
| F1 | 48.6 | 32.4 | 26.2 | 21.0 | 128.2 | 60 |
| G1 | 42.9 | 28.5 | 23.9 | 18.8 | 114.1 | 126 |
| H1 | 44.1 | 27.7 | 22.6 | 14.3 | 108.7 | 106 |
| I1 | 48.5 | 29.0 | 20.2 | 11.7 | 109.4 | 92 |
| J1 | 47.4 | 27.6 | 22.9 | 12.3 | 110.2 | 12 |
| K1 | 44.6 | 27.7 | 21.2 | 14.1 | 107.6 | 30 |
| L1 | 47.7 | 25.7 | 11.7 | 7.5 | 91.6 | 23 |
| M1 | 44.5 | 27.6 | 20.1 | 12.8 | 105 | 12 |

[1]Pressure Absorbency Index
[2]Vortex Time in seconds
*Average of 6 test values instead of 3

The superabsorbent materials described above in Tables 4 and 5 were incorporated into disposable diapers generally having the construction set forth in commonly assigned U.S. patent application Ser. No. 08/145,924, filed Oct. 29, 1993, by Tanzer et al., Now U.S. Pat. No. 5,411,497, issued May 2, 1995. More specifically, the diapers employed in the use test have the following construction.

The diapers were, again, generally identical to the commercially available HUGGIES UltraTrim Step 3 diapers with the exception that the absorbent pad employed in the UltraTrim Step 3 diaper is replaced with the retention portion described below.

The retention portion included an absorbent laminate and a distribution layer. The distribution layer was comprised of wood pulp fibers arranged in a T-shaped pad having generally the same dimensions as the absorbent pad (fluff and superabsorbent) of the UltraTrim Step 3 diaper and having an average basis weight of 300 grams per square meter. Sixty percent by weight of the wood pulp fibers were located in the front half (longitudinal) of the distribution layer, and the distribution layer was compressed to an average of 0.2 grams per cubic centimeter (taken under a load of 0.2 pound per square inch). The overall length of the distribution layer was 375 millimeters. A cellulose tissue having a basis weight of about 17 grams per square meter was wrapped around the distribution layer.

An absorbent laminate was placed on top (closer to the body of a wearer) of the distribution layer. The absorbent laminate comprised a 140 millimeter wide bottom cellulose tissue layer having a basis weight of 17 grams per square meter. Nine grams of superabsorbent material and 0.5 grams of wood pulp fiber were air formed onto the bottom tissue layer into a patterned area as depicted in FIGS. 2 and 3. Each pocket had rounded edges and was approximately 25 millimeters in length and 12 millimeters in width. As can be seen from FIGS. 2 and 3, the length (longer dimension) of a majority of the pockets corresponds to the machine direction of the product. Along the machine direction of the product, the rounded ends of immediately adjacent pockets were spaced apart by a distance of 6–7 millimeters. Across the transverse direction of the product (direction perpendicular to the machine direction) the pockets were spaced apart by a distance of about 6–7 millimeters. The overall length of the patterned area containing the pockets was 280 millimeters. As illustrated in FIG. 3, the patterned area was positioned towards the front of the diaper beginning about 25 millimeters from the front edge of the distribution layer. MA 140 millimeter wide top cellulose tissue layer having a basis weight of 21 grams per square meter was sprayed with uniform swirls of Cycloflex 70-3998 hot melt adhesive (commercially available from National Starch and Chemical Co., of Bridgewater, N.J.) at a level of about 15 grams per square meter and adhered to the bottom cellulose tissue. The overall length of the retention portion was 375 millimeters.

The resultant retention portion was sandwiched between a back sheet comprised of 1.25 mil polyethylene film (same as that employed in Example 1) and a top sheet comprised of a hydrophilized spunbond web of polypropylene fibers. The top sheet material was sized to be substantially coextensive with the diaper back sheet and was composed of polypropylene fibers having a fiber denier within the range of from about 2.9–3.3 denier. The fibers formed a nonwoven spunbonded web having a basis weight of about 22 grams per square meter. A surge management layer, composed of a bonded carded web, was attached to the body-side surface of the top sheet with a pattern of hot melt construction adhesive. The surge management material was the same as that employed in Example 1 and had a width of about 102 millimeters and extended along the entire length of the diaper. The diaper further comprised containment flaps, leg elastics, elastic waistbands, and the like as set forth in U.S. patent application Ser. No. 07/757,760 now U.S. Pat. No. 5,509,915.

Diapers having the construction set forth above and employing the superabsorbents described in Tables 4 and 5 were subjected to use testing as set forth in Example 1. The results of the diaper leakage testing are presented below in Table 6. The data in Table 6 is broken into three separate use tests. The data reported in Table 6 is the same type of data reported in Table 3 with the headings for the data (types of data) being the same and having the same meaning as that set forth in connection with Table 3.

TABLE 6

| Diaper | Super-absorbent[1] | % Overall Leaks | % 300 ml Leaks | % 90 ml Leaks | % 180 ml Leaks | % 270 ml Leaks |
|---|---|---|---|---|---|---|
| Use Test 6 | | | | | | |
| 1* | A1 | 13.1 | 11.9 | 3.6 | 13.8 | 30.0 |
| 2 | B1 | 6.8 | 5.5 | 3.3 | 2.8 | 18.2 |

TABLE 6-continued

| Diaper | Super-absorbent[1] | % Overall Leaks | % 300 ml Leaks | % 90 ml Leaks | % 180 ml Leaks | % 270 ml Leaks |
|---|---|---|---|---|---|---|
| 3 | C1 | 6.8 | 5.5 | 2.1 | 5.4 | 17.5 |
| 4* | D1 | 12.9 | 9.9 | 3.9 | 12.9 | 21.7 |
| 5* | E1 | 10.5 | 9.0 | 2.5 | 9.2 | 25.8 |
| Use Test 7 | | | | | | |
| 1 | F1 | 9.2 | 7.6 | 1.0 | 7.1 | 25.9 |
| 2 | G1 | 9.2 | 8.4 | 2.9 | 6.9 | 24.5 |
| 3 | H1 | 9.3 | 7.8 | 1.0 | 5.0 | 30.9 |
| 4 | I1 | 8.2 | 7.6 | 1.6 | 8.6 | 24.1 |
| 5 | J1 | 7.9 | 6.6 | 0.4 | 7.1 | 19.2 |
| 6 | K1 | 9.9 | 7.8 | 0.0 | 8.1 | 23.6 |
| 7* | L1 | 10.6 | 8.9 | 0.7 | 10.1 | 26.0 |
| Use Test 8 | | | | | | |
| 1 | G1 | 6.9 | 6.4 | 1.7 | 5.6 | 20.8 |
| 2 | H1 | 6.6 | 6.3 | 1.6 | 8.2 | 15.1 |
| 3 | I1 | 9.9 | 9.6 | 3.8 | 12.4 | 19.2 |
| 4 | J1 | 7.2 | 6.9 | 1.4 | 9.6 | 16.3 |
| 5 | K1 | 8.1 | 7.7 | 1.0 | 8.9 | 25.3 |
| 6* | L1 | 10.4 | 9.6 | 1.6 | 11.4 | 32.5 |
| 7 | M1 | 9.2 | 7.8 | 1.6 | 11.4 | 18.2 |

[1]Superabsorbent used, selected from Table 4
*Not an example of the present invention As can be seen from reference to Table 6, Use Tests 6, 7, and 8 generally indicate that absorbent composites according to the present invention generally perform better than absorbent composites employing superabsorbent materials outside of the present invention. Specifically, diapers number 1, 4 and 5 in Use Test 6 are seen to demonstrate the highest percent overall leaks, percent 300 ml leaks, and percent 180 ml leaks, which, as set forth above, is believed to be the best indication of performance. Similarly, diaper number 7 of use test 7 and diaper number 6 of use test 8 are seen to demonstrate the highest or near highest percent overall leaks, percent 300 ml leaks, and percent 180 ml leaks.

Use Tests 7 and 8 demonstrate that superabsorbent materials possessing a range of Pressure Absorbency Index and Vortex Times are generally suitable for use in the present invention. Further, comparison of diapers 4 and 5 in Use Test 7 and diapers 3 and 4 in Use Test 8 illustrates the importance of Vortex Time. Specifically, the superabsorbent materials used in the diapers have generally the same Pressure Absorbency Index (109.4 and 110.2). However, he superabsorbent material used in diaper 4 of Use Test 7 and diaper 3 of Use Test 8 has a Vortex Time of 92 seconds. The superabsorbent material used in diaper 5 of Use Test 7 and diaper 4 of Use Test 8 has a Vortex Time of 12. As can be seen from reference to able 6, the diaper employing the superabsorbent material having the lower Vortex Time (12) generally performs better than the diaper employing the superabsorbent material having the higher Vortex Time.

Comparison of diapers 3 and 5 of use test 7 similarly demonstrates the importance of Vortex Time. Comparison of diapers 2 and 4 of use test 8 neither supports nor contradicts the belief that Vortex Time is an important characteristic of superabsorbent material.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A method of testing superabsorbent materials for their suitability for use in absorbent composites to be included in disposable absorbent garments, said absorbent composites comprising from about 30 to about 100 weight percent of superabsorbent material, said method comprising the steps of (a) determining the absorbency under load characteristics of the superabsorbent materials at restraining forces of 0.01, 0.29, 0.57, and 0.90 pounds per square inch, (b) determining the total of the absorbency under load characteristics at each said restraining force for each superabsorbent material, and (c) choosing as suitable a superabsorbent material for which the total of said absorbency under load characteristics is at least about 110.

(c) choosing as suitable a superabsorbent material for which the total of said absorbency under load characteristics is at least about 110.

2. The method according to claim 1 wherein the superabsorbent material chosen has a total of said absorbency under load characteristics of at least about 120.

3. The method according to claim 1 wherein the superabsorbent material chosen has a total of said absorbency under load characteristics of at least about 140.

4. The method according to claim 1 wherein the superabsorbent material chosen also has a 16-hour extractables level of less than about 10 weight percent.

5. The method according to claim 1 wherein a superabsorbent material chosen also has a 16-hour extractables level of less than about 7 weight percent.

6. The method according to claim 1 wherein a superabsorbent material chosen also has a 16-hour extractables level of less than about 3 weight percent.

* * * * *